US006703238B2

(12) United States Patent
Bachovchin et al.

(10) Patent No.: US 6,703,238 B2
(45) Date of Patent: Mar. 9, 2004

(54) METHODS FOR EXPANDING ANTIGEN-SPECIFIC T CELLS

(75) Inventors: William Bachovchin, Melrose, MA (US); Barbara Wallner, Weston, MA (US)

(73) Assignee: Point Therapeutics, Inc., Boston, MA (US)

( * ) Notice: Subject to any disclaimer, the term of this patent is extended or adjusted under 35 U.S.C. 154(b) by 0 days.

(21) Appl. No.: 09/812,528

(22) Filed: Mar. 20, 2001

(65) Prior Publication Data

US 2001/0018210 A1 Aug. 30, 2001

Related U.S. Application Data

(63) Continuation of application No. 09/162,934, filed on Sep. 29, 1998, now Pat. No. 6,258,597.
(60) Provisional application No. 60/060,306, filed on Sep. 29, 1997.

(51) Int. Cl.[7] .............................. C12N 5/00; C12N 5/02
(52) U.S. Cl. ..................... 435/325; 435/377; 435/383; 424/184.1; 424/195.11; 514/2
(58) Field of Search ................... 435/325, 377, 435/383; 424/184.1, 195.11; 514/2

(56) References Cited

U.S. PATENT DOCUMENTS 4,318,904 A    3/1982    Shaw et al.

(List continued on next page.)

FOREIGN PATENT DOCUMENTS

| DD | 158109 | 12/1982 |
|---|---|---|
| DD | 270382 A1 | 7/1989 |
| DD | 296075 A5 | 11/1991 |
| EP | 0356223 A2 | 2/1990 |
| EP | 0371467 A2 | 6/1990 |
| EP | 0471651 A2 | 2/1992 |
| EP | 0481311 A2 | 4/1992 |
| EP | 0615978 A1 | 9/1994 |
| EP | 0420913 B1 | 11/1995 |
| EP | 0688788 A1 | 12/1995 |
| WO | WO 89/03223 | 4/1989 |
| WO | WO 91/16339 | 10/1991 |
| WO | WO 91/17767 | 11/1991 |
| WO | WO 92/12140 | 7/1992 |
| WO | WO 92/17490 | 10/1992 |
| WO | WO 93/02057 | 2/1993 |
| WO | WO 93/05011 | 3/1993 |
| WO | WO 93/08259 | 4/1993 |
| WO | WO 93/10127 | 5/1993 |
| WO | WO 93/16102 | 8/1993 |
| WO | WO 94/03055 | 2/1994 |
| WO | WO 94/09132 | 4/1994 |
| WO | WO 94/20526 | 9/1994 |
| WO | WO 94/25873 | 11/1994 |
| WO | WO 94/28915 | 12/1994 |
| WO | WO 94/29335 | 12/1994 |

(List continued on next page.)

OTHER PUBLICATIONS

Database Biosis, AN 1993:388665. Lotsova et al. Journal of Immunology, (1993) vol. 150, No. 12, pp. 5263–5269.*

(List continued on next page.)

*Primary Examiner*—Michael Borin
(74) *Attorney, Agent, or Firm*—Wolf, Greenfield and Sacks, P.C.

(57) ABSTRACT

Methods for expanding antigen-specific T cells in vitro are provided. The methods involve contacting hematopoietic precursor or progenitor cells with a heteroconjugate containing an inhibitor of dipeptidyl peptidase (DPIV) attached to an antigenic peptide, optionally with a culture step to expand T cells with a DPIV inhibitor. The culture may be performed in the absence of exogenously provided cytokines.

19 Claims, 5 Drawing Sheets

U.S. PATENT DOCUMENTS

| | | | |
|---|---|---|---|
| 4,443,609 A | 4/1984 | Oude Alink et al. | |
| 4,499,082 A | 2/1985 | Shenvi et al. | |
| 4,582,821 A | 4/1986 | Kettner et al. | |
| 4,636,492 A | 1/1987 | Kettner et al. | |
| 4,644,055 A | 2/1987 | Kettner et al. | |
| 4,652,552 A | 3/1987 | Kettner et al. | |
| 4,935,493 A | 6/1990 | Bachovchin et al. | |
| 4,963,655 A | 10/1990 | Kinder et al. | |
| 5,093,477 A | 3/1992 | Mölling et al. | |
| 5,187,157 A | 2/1993 | Kettner et al. | |
| 5,215,926 A | 6/1993 | Etchells, III et al. | |
| 5,242,904 A | 9/1993 | Kettner et al. | |
| 5,250,720 A | 10/1993 | Kettner et al. | |
| 5,288,707 A | 2/1994 | Metternich | |
| 5,296,604 A | 3/1994 | Hanko et al. | |
| 5,329,028 A | 7/1994 | Ashkenzi et al. | |
| 5,378,624 A | 1/1995 | Berenson et al. | |
| 5,384,410 A | 1/1995 | Kettner | |
| 5,444,049 A | 8/1995 | de Nanteuil et al. | |
| 5,462,928 A | 10/1995 | Bachovchin et al. | |
| 5,506,130 A | 4/1996 | Peterson et al. | |
| 5,527,923 A | 6/1996 | Klingler et al. | |
| 5,543,396 A | 8/1996 | Powers et al. | |
| 5,554,728 A | 9/1996 | Basava et al. | |
| 5,635,386 A | 6/1997 | Palsson et al. | |
| 5,635,387 A | 6/1997 | Fei et al. | |
| 5,646,043 A | 7/1997 | Emerson et al. | |
| 5,965,532 A | * 10/1999 | Bachovchin | 514/12 |
| 6,258,597 B1 | 7/2001 | Bachovchin et al. | |

FOREIGN PATENT DOCUMENTS

| | | |
|---|---|---|
| WO | WO 95/11689 | 5/1995 |
| WO | WO 95/12618 | 5/1995 |
| WO | WO 95/15309 | 6/1995 |
| WO | WO 95/29190 | 11/1995 |
| WO | WO 95/29691 | 11/1995 |
| WO | WO 95/34538 | 12/1995 |
| WO | WO 96/40263 | 12/1996 |
| WO | WO 96/40858 | 12/1996 |
| WO | WO 98/00439 | 1/1998 |
| WO | WO 98/50046 | 11/1998 |
| WO | WO 98/50066 | 11/1998 |
| WO | WO 99/16864 | 4/1999 |

OTHER PUBLICATIONS

Database Caplus, DN 123:81521 Kaehne et al. Immunology Letters (1995), 46(1,2), 189–93.*

Database Caplus, DN 122:211752. Reinhold et al. Immunobiology (1994), 192(1–2), 121–36.*

Database Caplus, DN 120:214808. Hegen et al. Immunobiology (1993), 189(5), 483–93.*

Colowick, S. et al., "Methods in Enzymology", pp. 220–225.

Cordes, E., et al., "Transition States for Hydrolysis of Acetals, Ketals Glycosides, and Glycosylamines", Chapter 11, pp. 429–465.

Thompson, R., "Use of Peptide Aldehydes to Generate Transition–State Analogs of Elastase", *Biochemistry,* (1973), 12:1:47–51.

Baugh, R., et al., "Proteinases and Tumor Invasion", (1980), 165:157–179.

Bodanszky, M., "Principles of Peptide Synthesis", *Springer–Verlag,* (1984), vol. 16.

Bodanszky, M., "The Practice of Peptide Synthesis", *Springer–Verlag,* (1984) vol. 21.

Matteson, D., et al., "Synthesis and Properties of Pinanediol – Am Ido Boronic Esters" *Organometallics,* (1984), 3:1284–1288.

Powers, C., et al., "Elastase Inhibitors for Treatment of Emphysema—NHLBI Workshop Summary", *US Dept. of Health and Human Services,* (1985), 1097–1100.

Yoshimoto, T., et al., "Comparison of Inhibitory Effects of Prolinal–Containing Peptide Derivates on Prolyl . . . ", (1985) 98:975–979.

Kettner, C.A., et al., "Kinetic Properties of the Binding of Alpha–Lytic Protease to Peptide Boronic Acids", *Biochemistry,* (1988), 27, 7682–7688.

Tam, J.P., "Synthetic Peptide Vaccine Design: Synthesis and Properties of a High–Density Multiple Antigenic Peptide System", *Proc Natl Acad Sci U S A ,* (1988), 85:5409–5413.

Bailey, P.D., "An Introduction to Peptide Chemistry", *Wiley Publishers,* (1990), 1–81.

Kettner, C.A. and Shenvi, A.B., "Peptide Boronic Acid Inhibitors of Trypsin–Like Proteases, Their Preparation and Use as Anticoagulants and Inflammation Inhibitors", *Chemical Abstract Onlys,* (1990), 112:80 (91790c).

Bachovchin, W.W., et al., "Inhibition of IGA1 Proteinases from Neisseria Gonorrhoeae and Hemophilus Influenzae by Peptide Prolyl Boronic Acids", *J Biol Chem,* (1990), 265: 3738–3743.

Kinder D.H., et al., "Analogues of Carbamyl Aspartate as Inhibitors of Dihydroorotase: Preparation of Boronic Acid Transition–State Analogues and A Zinc Chelator Carbamylhomocysteine, Carbamylhomocysteine", *J Med Chem,* (1990), 33:819–823.

Flentke, G.R., et al., "Inhibition of Dipeptidyl Aminopeptidase IV (DP–IV) by XAA–Boropro Dipeptides and Use of These Inhibitors to Examine the Role of DP–IV in T–Cell Function", *Proc Natl. Acad Sci U S A,* (1991), 88:1556–1559.

Schon, E., et al., "Dipeptidyl Peptidase IV in the Immune System", *Biol Chem Hoppe–Seyler,* (1991), 372:305–311.

Kubota, T., et al., "Involvement of Dipeptidyl Peptidase IV In An In Vivo Immune Response", *Clin Exp Immunol,* (1992), 89:192–197.

Guthiel, W.G., et al., "Separation of L–Pro–DL–Boropro Into Its Component Diastereomers and Kinetic Analysis of Their Inhibition of Dipeptidyl Peptidase IV. A New Method for the Analysis of Slow, Tight–Binding Inhibition", *Biochemistry,* (1993), 32:8723–8731.

Kelly, T.A., et al., "Immunosuppressive Boronic Acid Dipeptides: Correlation Between Conformation and Activity", *J Am Chem Soc,* (1993), 115:12637–12638.

Songyang, Z., et al., "SH2 Domains Recognize Specific Phosphopeptide Sequences", *Cell,* (1993), 72:767–778.

Subramanyam, M., et al. , "Mechanism of HIV–1 TAT Induced Inhibition of Antigen–Specific T Cell Responsiveness", *J Immunol,* (1993), 150:2544–2553.

Demuth, H.U., et al., "Design of (Omega–N–(O–Acyl)Hydroxy Amid) Aminodicarboxylic Acid Pyrrolidides as Potent Inhibitors of Proline–Specific Peptidases", *FEBS Lett,* (1993), 320:23–27.

Janeway, C., et al., "Immunobiology—The Immune System in Health and Disease", *Current Biology LTD,* (1994), Chapter 12, pp. 1–35.

Brady, L., and Dodson, G., "Reflections on a Peptide", *Nature,* (1994), 368:692–693.

Nicola, N, et al., "Guidebook to Cytokines and Their Receptors", *Sambrook and Tooze Publication,* (1994), pp. 1–257.

Perstorp Biotec Company, "Molecular Biology Catalog", (1994).

Jameson, B.A., et al., "A Rationally Designed CD4 Analogue Inhibits Experimental Allergic Encephalomyelitis", *Nature,* (1994), 368:744–746—Abstract Only.

Mosmann, T.R., "Cytokine Patterns During the Progression to Aids", *Science,* (1994), 265:193–194.

Seed, B., "Making Agonists of Antagonists", *Chemistry & Biology,* (1994), 1:125–129.

Austin, D.J., et al., "Proximity Versus Allostery: The Role of Regulated Protein Dimerization in Biology", *Chemistry & Biology,* (1994), 1:131–136.

Sudmeier, J.L., et al., "Solution Structures of Active and Inactive Forms of the DP IV (CD26) Inhibitor Pro–Boropro Determined by NMR Spectroscopy", *Biochemistry,* (1994), 33:12427–12438.

Kubota, T., et al., "Dipeptidyl Peptidase IV (DP IV) Activity in Serum and On Lymphocytes of MRL/Mp–lpr/lpr Mice Correlates with Disease Onset", *Clin Exp Immunol,* (1994), 96:292–296.

Snow, R.J., et al., "Studies on Proline Boronic Acid Dipeptide Inhibitor of Dipeptidyl Peptidase IV: Identification of a Cyclic Species Containing A B–N Bond", *J. Am. Chem Soc,* (1994), 116:10860–10869.

Günther, U.L., et al., "Solution Structures of the DP IV (CD26) Inhibitor Val–BoroPro Determined by NMR Spectroscopy", *Magnetic Resonance in Chem,* (1995), 33:959–970.

Subramanyam, M., et al., "CD26, AT–Cell Accessory Molecule Induction of Antigen–Specific Immune–Suppression by Inactivation of CD26: A Clue to the Aids Paradox?", in *Dipeptidyl Peptidase IV(CD26) in Metabolism and Immune Response,* (1995), Ed. B. Fleischer: 155–162.

Schmitz T, et al., "Potentiation of the Immune Response in HIV–1+Individuals", *J Clin Invest,* (1996), 97:1545–1549.

Aguila, H.L., et al., "From Stem Cells to Lymphocytes: Biology and Transplantation", *Immun Rev,* (1997), 157:13–40.

Dupont, B., "Immunology of Hematopoietic Stem Cell Transplantation: A Brief Review of Its History", *Immun Rev,* (1997), 157:5–12.

Bodansky, M., "Peptide Chemistry, A Practical Textbook", *Springer–Verlag,* (1988) 1–9.

Boros, L.G., et al., "Fluoroolefin Peptide Isosteres–Tools for Controlling Peptide Conformations", *Tetrahedron Letters,* (1994), 35:6033–6036.

Goodman, M., and Chorev, M., "On the Concept of Linear Modified Retro–Peptide Structures", *Accounts of Chemical Research,* (1979), 12:1–7.

Guichard, G., et al., "Partially Modified Retro–Inverson Pseudopeptides as Non–Natural Ligands for the Human Class I Histocompatibility Molecule HLA–A2, *J Med Chem,* (1996), 39:2030–2039.

Jardtzky, T.S., et al., Three–Dimensional Structure of a Human Class II Histocompatibility Molecule Complexed with Superantigen, *Nature,* (1994), 368:711–718.

Zimmerman, D.H., et al., "A New Approach to T–Cell Activation: Natural and Synthetic Conjugates Capable of Activating T Cells", *Vaccine Res,* (1996), 5:91–102.

Zimmerman, D.H., et al., "Immunization with Peptide Heteroconjugates Primes a T Helper Cell . . . " *Vaccine Res,* (1996), 5:103–118.

Welch, J.T., and Lin J., Fluoroolefin Containing Dipeptide Isoteres as Inhibitors of Dipeptidyl Peptidase IV (CD26), *Tetrahedron,* (1995), 52:291–304.

Duke–Cohan, J.S., et al., "Targeting of an Activated T–Cell Subset Using a Bispecific Antibody–Toxin Conjugatedirected Against CD4 and CD26", *Blood,* (1993), 82:2224–2234. (Abstract Only) directed against CD4 and CD26. Blood. 1993 Oct 1; 82(7): 2224–2234.

Kameoka, J., et al., "Direct Association of Adenosine Deaminase with a T Cell Activation Antigen, CD26", *Science,* (1993), 261:466–469. (Abstract Only).

Hegen, M., et al., "Function of Dipeptidyl Peptidase IV (CD26, TP103) in Tranfected Human T Cells", *Cell Immunol,* (1993), 146:249–260. (Abstract Only).

Hegen, M., et al., "Enzymatic Activity of CD26 (Dipeptidylpeptidase IV) is Not Required for its Signalling Function in T Cells", *Immunobiology,* (1993), 189:483–493. (Abstract Only).

Tanaka, T., et al., "The Costimulatory Activity of the CD26 Antigen Requires Dipeptidyl Peptidase IV Enzymatic Activity", *Proc Natl Acad Sci U S A,* (1993), 90:4586–4590. (Abstract Only).

Tanaka, T., et al., "Cloning and Functional Expression of the T Cell Activation Antigen CD26", *J Immunol,* (1992), 149:481–486. (Abstract Only).

Scharpe, S., et al., "Purified and Cell–Bound CD26: Enzymatic Inhibition, Antibody Binding Profile, and Expression on T Cells in Relation to Other Surface Markers" *Verh K Acad Geneeskd Belg,* (1994), 56:537–559. (Abstract Only).

Kameoka, J., et al., "Differential CD26–Mediated Activation of the CD3 and CD2 Pathways After CD6–Depleted Allogeneic Bone Marrow Transplantation", *Blood,* (1995), 85:1132–1137. (Abstract Only).

Mittrucker, H.W., et al., "The Cytoplasmic Tail of the T Cell Receptor Zeta Chain is Required for Signaling Via CD26", *Eur J Immunol,* (1995), 25:295–297. (Abstract Only).

Morimoto, C., et al., 1F7 "A Novel Cell Surface Molecule, Involved In Helper Function Of CD4 cells", *J. Of Im* Morimoto,m I *Immunol.* 143:34030–3439 (1989) and published erratum appears in *J. Immunology* 144 (5):2027 (Mar. 1990). Abstract Only.

Barton, R.W.J., et al., "Binding Of The T Cell Activation Monoclonal Antibody Ta1 To Dipeptidyl Peptidase IV", *Leukocyte Biology* 48:291–296 (1990). Abstract. *J. Of Leukocyte Biology* 48:291–296 (1990). Abstract Only.

Bristol L.A., et al., "Thymocyte Costimulating Antigen Is CD26 (Dipeptidyl–Peptidase IV), Co–stimulation Of Granulocyte, Macrophage, T Lineage Cell Proliferation Via CD26," *J. Of Immunol.* 149:367–372 (1992). Abstract Only.

Bristol, L.A., et al., "Characterization Of A Novel Rat Thymocyte Costimulating Antigen By The Monoclonal Antibody 1.3", *J. Of Immunol.* 148:332–338 (1992). Abstract Only.

Fleisher, B., et al., "Triggering Of Cytotoxic T Lymphocytes And NK Cells Via The Tp103 Pathway Is FIFF Dependent On the Expression Of The T Cell Receptor/CD3 Complex", *J. Of Immunol.* 141:1103–1107 Abstract Only.

Hegen, M., et al., "The T Cell Triggering Molecule Tp103 . . . " *J. Immunol.* 144:2980–2914 (1990). Abstract Only.

Darmoul, D., et al., "Dipeptidyl Peptidase IV (CD26) Gene Expression In Enterocyte–like Colon Cancer Cell Lines HT–29 And Caco–2: Cloning Of The Complete Human Coding Sequence And Changes Of Dipeptidyl Peptidase IV mRNA Levels During Cell Differentiation," *J. Of Biological Chemistry* 267:220–2208 (1992). Abstract Only.

Tanaka, T., et al., "Cloning And Functional Expression Of The T Cell Activation Antigen CD26", *J. Of Immunol.* 149:481–486 (1992); published erratum appears in *J. Immunol.* 50(5): 2090 (Mar. 1993). Abstract Only.

Heins, J., et al., "Mechanism Of Proline–Specific Proteinases: (I) Substrate Specificity of Dipeptidyl Peptidase IV From Pig Kidney And Proline–Specific Endopeptidase From Flavobacterium Meningosepticum", *Biochimica Et Biophysica Acta* 954:161–169 (1988). Abstract Only.

Schon, E., et al., "Dipeptidyl Peptidase IV In The Immune System. Effects of Specific Enzyme Inhibitors On Activity Of Dipeptidyl Peptidase IV And Proliferation Of Human Lymphocytes", *Biological Chemistry Hoppe Seyler* 372:305–311 (1991). Abstract Only.

Schon, E., et al., "The Dipeptidyl Peptidase IV, A Membrane Enzyme Involved In The Proliferation . . . Lymphocytes", *Biomedica Biochimica Acta* 44(1985). Abstract Only.

Schon, E., et al., "Dipeptidyl Peptidase IV In Human T Lymphocytes. An Approach To The Role Of A Membrane Peptidase In The Immune System", *Biomedica Biochimica Acta* 45:1523–1528 (1986) Abstract Only.

Schon, E., et al., "The Role Of Dipeptidyl Peptidase IV In Human T Lymphocyte Activation. Inhibitors And Antibodies Against Dipeptidyl Peptidase IV Suppress Lymphocyte Proliferation And Immunoglobulin Synthesis In Vitro", *Eur. J Of Immunol.* 17:1821–1826 (1987). Abstract Only.

Freeman, et al., "*Clinical & Experimental Immunology* " 88 (2):275–279 (May 1992). Abstract Only.

Perry, et al., *Eur. J. Of Immunol.* 26(1): 136–141 (Jan. 1996). Abstract Only.

Goodstone, et al., *Annals Of The Rheumatic Diseases* 55(1):40–46 (Jan. 1996). Abstract Only.

Hall, et al., *Seminars In Dermatology,* 10(3):240–245 (Sep. 1991). Abstract Only.

Karges, et al., *Molecular Aspects Of Medicine* 16(2):29–213 (1995). Abstract Only.

Short, et al., *Nephrol Dial Transplant* (Supp. 1) pgs. 1–121 (1992). Abstract Only.

Kalluri, et al., *J. Of The American Society Of Nephrology* 6(4):1178–1185 (Oct. 1995). Abstract Only.

Mullins, et al., *J. Of Clinical Investigation* 96 (1): 30–37 (Jul. 1996). Abstract Only.

El Far, et al., *J. Of Neurochemistry,* 64(4): 1696–1702 (Apr. 1995). Abstract Only.

James, et al., *Clinical & Experimental Rheumatology,* 13 (3):299–305 (May–Jun. 1995). Abstract Only.

Van Noort, et al., *Nature* 375 (6534):798–801 (Jun. 29, 1995). Abstract Only.

Protti, et al., *Immunol. Today* 14 (7): 363–368 (Jul. 1993). Abstract Only.

Linington, et al., *Eur. J. Of Immunol.* 22(7): 1813–1817 (Jul. 1992). Abstract Only.

Chan, et al., *Archives Of Ophthalmology* 113(5): 597–600 (May 1995). Abstract Only.

Liu, et al., *J. Of Immunol.* 155 (11):5449–5454 (Dec. 1995). Abstract Only.

Uibo, et al., *J. Of Autoimmunity* 7(3): 399–411 (Jun. 1994). Abstract Only.

Kokawa, et al., *Eur. J. Of Hematology* 50 (2): 74–80 (1993). Abstract Only.

Daw, et al., *J. Of Immunol.* 156 (2): 818–825 (Jan. 15, 1996). Abstract Only.

Chazenblak, et al., *J. Of Clinical Investigation* 92 (1):62–74 (Jul. 1993). Abstract Only.

Hart, et al., *Pharmaceutical Biotechnology* 6:821–845 (1995). Abstract Only.

Lopez, et al., *Vaccine* 12 (7):585–591 (1994). Abstract Only.

Reynolds, et al., *J. Of Immunol.* 152 (1):193–200 (Jan. 1, 1994). Abstract Only.

Nardelli, et al., *J. Of Immunol.* 148 (3):914–920 (Feb. 1, 1992). Abstract Only.

Darcy, et al., *J. Of Immunol.* 149 (11):3636–3641 (Dec. 1, 1992). Abstract Only.

Ritu, et. al., *Vaccine* 10 (11): 761–765 (1992). Abstract Only.

Ikagawa, et al., *J. Of Allergy & Clinical Immunol.* 97 (1Pt 1): 53–64 (Jan. 1996). Abstract Only.

Brander, et al., *J. Of Immunol.* 155 (5):2670–2678 (Sep. 1, 1995). Abstract Only.

O'Brien, et al., *Immunology* 86 (2):176–182 (Oct. 1995). Abstract Only.

Zhu et al., *J. Immunol* 155(10), pgs. 5064–5073 (Nov. 1995). Abstract Only.

Dudler, et al., *Eur. J. Of Immunol.* 25 (2):538–542 (Feb. 1995). Abstract Only.

Bungy, et al., *Eur. J. Of Immunol.* 24 (9):2098–213 (Sep. 1994). Abstract Only.

Shimojo, et al., *Int'l. Archives Of Allergy & Immunol.* 105 (2):155–161 (Oct. 1994). Abstract Only.

Kelly, T.A., et al., "The Efficient Synthesis And Simple Resolution Of A Proline Boronate Ester Suitable For Enzyme Inhibition Studies", *Tetrahedron* 49:1009–1016 (1993). Abstract Only.

Watson, J.D., "Continuous Proliferation Of Murine Antigen Specific Helper T Lymphocytes In Culture", *J. Of Experimental Medicine* 150:1510 (1979). Abstract Only.

Kuchroo, V.K., et al., "Induction Of Experimental Allergic Encephalomyelitis By Myelin Proteolipid–Protein–Specific T Cell Clones And Synthetic Peptides", *Pathobiology* 59:305–312 (1991). Abstract Only.

Kuchroo, V.K., et al., "T–cell Receptor Alpha Chain Plays a Critical Role In Antigen–Specific Suppressor Cell Function", *Proceedings Of The Nat'l. Academy Of Sciences Of The United States Of America* 88:8700 88:8700–8704 (1991). Abstract Only.

Kuchroo, V.K., et al., "Experimental Allergic Encephalomyelitis Medicated By Cloned T Cells Specific For A Synthetic Peptide of Myelin Proteolipid Protein. Fine Specificity And T Cell Receptor V Beta Usage", *J. Of Immunol.* 148:3776–3782 (1992). Abstract Only.

Kuchroo, V.K., et al., "Cytokines And Adhesion Molecules Contribute To The Ability Of Myeline Proteolipid Protein–Specific T Cell Clones To Mediate Experimental Allergic Encephalomyelitis", *J. Of Immunol.* 151:4371–4382 (1993). Abstract Only.

Kuchroo, V.K., et al., "T Cell Receptor (TCR) Usage Determines Disease Susceptibility In Experimental Autoimmune Encephalomyelitis: Studies with TCR V Beat *.2 Transgenic Mice", *J. Of Experimental Medicine* 179:1659–1664 (1994). Abstract Only.

Kuchroo, V.K. et al., "A Single TCR Antagonist Peptide Inhibits Experimental Allergic Encephalomyelitis Mediated By A Diverse T Cell Repertoire", *J. Of Immunol..* 153:3326–3336 (1994). Abstract Only.

Jorgensen, J.L., et al., "Molecular Components Of T–Cell Recognition," *Annu. Rev. Immunol.* 10:835–873 (1992). Abstract Only.

Wyse–Coray, T., et al., "Use Of Antibody/Peptides Constructs Of Direct Antigenic Peptides To T Cells: Evidence For T Cells Processing And Presentation", *Cellular Immunol.*, 139 (1):268–73 (1992). Abstract Only.

Panina–Bordignon, P., et al., "Universally Immunogenic T Cell Epitopes: Promiscuous Binding To Human MHC Class II And Promiscuous Recognition By T Cells", *Eur. J. Immunol.* 19:2237–2242 (1989). Abstract Only.

Ebenbichler, C., et al., "Structure–function Relationships Of The HIV–I Envelope V3 Loop Tropism Determinant: Evidence For Two Distinct Conformation", *Aids* 7:639–46 (1993). Abstract Only.

Linsley, P.S., et al., "Effects Of Anti–gp120 Monoclonal Antibodies On CD4 Receptor Binding By The Env Protein Of Human Immunodeficieny Virus Type 1", *J. Of Virology* 62:3695–3702 (1988). Abstract Only.

Rini, J.M., et al., "Crystal Structure Of A Human Immunodeficiency Virus Type 1 Neutralizing Antibody, 50.1, In Complex With Its V3 Loop Peptide Antigen", *Proceedings Of The Nat'l. Academy Of Sciences Of The United States Of America* 90:6325–9 (1993). Abstract Only.

Subramanyam, W.G., et al., "Mechanism Of HIV–1 Tat Induced Inhibition Of Antigen–Specific T Cell Responsiveness", *J. Of Immunol.* 150:2544–2553 (1993). Abstract Only.

Dang, N.H., et al., "Cell Surface Modulation Of CD26 By Anti–1F7 Monoclonal Antibody: Analysis Of Surface Expression And Human T Cell Activation", *J. Of Immunol.* 145:3963–3971 (1990). Abstract Only.

De Caestecker, M.P., et al., "The Detecton Of Intercytoplasmic Interleukin 1 (Alpha) Expression In Human Monocytes Using Two Colour Immunofluorescence Flow Cytometry", *J. Immunol. Methods* 154:11–20 (1992). Abstract Only.

Fauci, A.S., "The Human Immunodeficiency Virus: Infectivity And Mechanisms Of Pathogenesis", *Science* 239:617–722 (1988). Abstract Only.

Kinder, D., et al., "Analogues of Carbamyl Aspartate as Inhibitors . . . " *J. Med. Chem,* (1990), 33:819–823.

Snow, R., et al., "Studies on Proline Boronic Acid Dipeptide Inhibityors of Dipeptidyl . . . " *J. Med. Chem,* (1990), 116:10860–10869.

Wijdenes et al., "Monoclonal Antibodies (mAb) against gp130 Imitating Cytokines Which Use the gp130 for Signal Transduction", (Jul., 1995), p. 303.

Blumenstein et al., "Synthetic Non–Peptide Inhibitors of HIV Protease," vol. 163, No. 2 (1989), pp. 980–987.

Luftig et al., "Update on Viral Pathogenesis," ASM News (1990) vol. 56, No. 7, pp. 366–368.

Jiang et al., "Inhibition of Human Immunodeficiency Virus Type 1 Infection in a T–Cell Line (CEM) by New Dipeptidyl–Peptidase IV (CD26) Inhibitors," *Res. Virol.* (2997), vol. 148, pp. 255–266.

Coutts et al., "Structure–Activity Relationships of Boronic Acid Inhibitors of Dipeptidyl Peptidase IV, 1. Variation of the $P_2$ Position of $X_{zz}$–boroPro Dipeptides," *J. Med. Chem.* (1996), vol. 39, pp. 2087–2094.

Ostresh et al., "Generation of Use Of Nonsupport–Bound Peptide and Peptidomimetic Combinatorial Libraries," *Methods in Enzymology,* (1996) vol. 267, pp. 220–234.

Bristol, L, et al., "Inhibition of CD26 Enzyme Activity with Pro–boropro Stimulates Rat Granulocyte/Macrophage Colony Formation and Thymocyte Proliferation in Vitro," *Blood,* vol. 85, No. 12 (1995), pp. 3602–3609.

Ansorge S., et al., "CD26/Dipeptidyl Peptidase IV in Lymphocyte Growth Regulation," *Advances in Medicine and Biology,* (1997), vol. 421, pp. 127–140.

Reinhold, Dirk, et al., "Inhibitors of Dipeptidyl PeptidaseIV (DP IV, CD26) Induces Secretion of Transforming Growth Factor–β1 . . . ", *Immunology Letters, 58(1997), pp. 29–35.*

\* cited by examiner

METHODS FOR EXPANDING ANTIGEN-SPECIFIC T CELLS

RELATED APPLICATIONS

This application is a continuation of U.S. Ser. No. 09/162,934, filed Sep. 29, 1998, now U.S. Pat. No. 6,258,597, which claims priority under U.S.C. §119(e) from U.S. Provisional Patent Application Serial No. 60/060,306, filed Sep. 29, 1997, entitled "STIMULATION OF HEMATOPOIETIC CELLS IN VITRO," the entire contents of which applications are incorporated herein by reference.

FIELD OF THE INVENTION

This invention relates to the use of agents which bind to dipeptidyl peptidase IV (DPIV, also known as CD26) for the stimulation of hematopoietic cells in vitro

BACKGROUND OF THE INVENTION

Bone marrow transplantation is widely used with patients undergoing high dose chemotherapy or radiation therapy. The dose limiting side effects of chemotherapy and radiation therapy are their deleterious effects on hematopoietic cells through destruction of the bone marrow cells which are the precursor cells for all hematopoietic cells. This damage to the marrow results in myelosuppression or myeloablation, rendering patients susceptible to opportunistic infections for a prolonged period of time. Bone marrow transplantation involves the infusion of early bone marrow progenitor cells that have the ability to re-establish the patients' hematopoietic system, including the immune system. Transplantation decreases the time normally required for the restoration of the immune system after chemotherapy or radiation therapy and, thus, the time of risk for opportunistic infections.

Bone marrow cells contain totipotent stem cells which give rise to hematopoietic cells of all lineages including the lymphoid, myeloid and erythroid lineages. Stem cells have the ability to renew themselves as well as to differentiate into progenitor cells of all hematopoietic lineages. Progenitor cells retain the ability to proliferate and give rise to differentiated cells of all lineages. Differentiated cells lose the ability to proliferate and exhibit morphological characteristics specific for their lineages (such as macrophages, granulocytes, platelets, red blood cells, T cells and B cells). Stem cells and progenitor cells express CD34 on their surface while differentiated cells do not. Bone marrow includes stem cells as well as progenitor cells of the lymphoid (T and B cells), myeloid (granulocytes, macrophages) and erythroid (red blood cells) lineages.

For use in bone marrow transplants, hematopoietic precursor cells can be derived either from the cancer patient (autologous transplant) or from a histocompatible donor (allogeneic donor). These cells can be isolated from bone marrow, peripheral blood or from umbilical cord blood. In all cases, cells are harvested before chemotherapy or radiation therapy. The number of progenitor cells that can be harvested at one time is small and, in many cases, is not sufficient for a successful transplant. Accordingly, several methods have been developed to expand, in vitro, bone marrow cells or progenitor cells obtained from blood aphereses or from umbilical cord blood.

The ability to expand these cells has helped advance bone marrow transplant technology as a viable adjunct therapy for cancer treatments that involve high doses of chemotherapy and/or irradiation. However, the existing methods for hematopoietic cell expansion require the addition of appropriate cytokines to permit the in vitro expansion of hematopoietic stem cells. The high cost of such growth factors has adversely affected the ability of those skilled in the art to expand hematopoietic cells in vitro for transplantation or other purposes. Accordingly, a need exists to develop new methods for expanding hematopoietic cells in vitro which do not require exogenously added cytokines to support cell growth and differentiation.

SUMMARY OF THE INVENTION

The present invention provides methods and compositions for stimulating the growth and differentiation of hematopoietic cells in vitro. Advantageously, the methods of the invention do not require the addition of exogenously added cytokines to support the stimulation of hematopoietic cells in vitro. Accordingly, the methods and compositions of the invention are useful for increasing the number of hematopoietic cells in vitro and/or causing the differentiation of early progenitor cells. Increasing the number and/or differentiation of hematopoietic cells in culture permits the characterization of such cells in culture under a variety of conditions, as well as the use of such cultured cells for the production of recombinant or naturally occurring molecules therefrom in vitro. In addition, the stimulated hematopoietic cells of the invention are useful for the treatment of disorders that are characterized by a reduced number of hematopoietic cells or their precursors in vivo. Such conditions occur frequently in patients who are immunosuppressed, for example, as a consequence of chemotherapy and/or radiation therapy for cancer.

The novelty of the invention is based, at least in part, on the discovery that inhibitors of dipeptidyl peptidase type IV ("DPIV") are useful for stimulating the growth and differentiation of hematopoietic cells in the absence of exogenously added cytokines or other growth factors or stromal cells. This discovery contradicts the dogma in the field of hematopoietic cell stimulation which provides that the addition of cytokines or cells that produce cytokines (stromal cells) is an essential element for maintaining and stimulating the growth and differentiation of hematopoietic cells in culture. (See, e.g., PCT Intl. Application No. PCT/US93/017173, published as WO94/03055).

According to one aspect of the invention, a method for stimulating hematopoietic cells to grow and differentiate in vitro is provided. The method involves: (1) contacting the hematopoietic cells with a sufficient amount of an inhibitor of a dipeptidyl peptidase type IV to increase the number and/or differentiation of hematopoietic cells when the cells are cultured in the presence of the inhibitor relative to the number and differentiation of hematopoietic cells that are present in a control culture that is not contacted with the inhibitor but is otherwise subjected to the same culture conditions as the hematopoietic cells which are cultured in the presence of the inhibitor; (2) culturing the hematopoietic cells in the presence of the inhibitor and in the absence of exogenously added cytokine under conditions and for a time sufficient to increase the number of hematopoietic cells and/or the differentiation of such cells relative to the number of hematopoietic cells that were present in the control culture; (3) culturing the hematopoietic cells in the presence or absence of stromal cells, and (4) culturing stromal cells in the presence of the DPIV inhibitor. In general, increasing the number of hematopoietic cells refers to increasing the number of cells by at least approximately 2-fold relative to the number of hematopoietic cells that are present when the cells initially are contacted with the inhibitor. In general, the number of cells that are present in a control culture that is not contacted with the inhibitor but is otherwise identically treated is approximately the same as the initial number of cells in the culture prior to contact with the inhibitor. Preferably, the number of hematopoietic cells are increased at least approximately 4-fold, 10-fold, 20-fold or, most preferably, at least 100-fold relative to the number of hematopoietic cells that are present when the hematopoietic cells initially are contacted with the inhibitor.

As used herein, hematopoietic cells includes hematopoietic stem cells, primordial stem cells, early progenitor cells, CD34+ cells, early lineage cells of the mesenchymal, myeloid, lymphoid and erythroid lineages, bone marrow cells, blood cells, umbilical cord blood cells, stromal cells, and other hematopoietic precursor cells that are known to those of ordinary skill in the art.

As used herein, an inhibitor of dipeptidyl peptidase type IV ("DPIV") generally refers to a molecule which inhibits the functional activity of the DPIV. Accordingly, the inhibitors of the invention include inhibitors of the enzymatic activity of the dipeptidyl peptidase type IV. Preferably, the inhibitors of the enzymatic activity of DPIV associate with the active site of DPIV by covalently bonding thereto or by forming an ionic interaction therewith. Such inhibitors include competitive inhibitors of DPIV, such as transition state analogs of DPIV, and non-competitive inhibitors of DPIV, such as fluoroalkylketones. Inhibitors of DPIV also include non-competitive inhibitors of DPIV which selectively bind to DPIV (covalently or via ionic interactions) at a site on the DPIV protein other than the active site and, thereby, inhibit the enzymatic activity of the DPIV. Such non-competitive inhibitors are one category of binding molecules which selectively bind to DPIV and have the ability to stimulate hematopoietic cells or thymocytes in vitro. Other binding molecules which selectively bind to DPIV and have the ability to stimulate hematopoietic cells include monoclonal antibodies, polyclonal antibodies and fragments of the foregoing which are capable of: (1) binding to DPIV, and (2) stimulating hematopoietic cells and/or thymocytes in vitro. The inhibitors of DPIV that are useful in the context of the present invention may be immobilized or insoluble form. In general, the foregoing inhibitors can be monovalent, bivalent, or multivalent. (See e.g., U.S. Ser. Nos. 08/671,756 and 08/837,305, entitled "Multivalent Compounds for Crosslinking Receptors and Uses Thereof" for a description of dimers and other conjugates of DPIV inhibitors.) The immobilized DPIV inhibitor may be immobilized to a variety of immobilization structures including conventional culture vessels (e.g., stirring flasks, stirred tank reactors, air lift reactors, suspension cell reactors, cell adsorption reactors and cell entrapment reactors, petri dishes, multi well plates, micro titer plates, test tubes, culture flasks, bags and hollow fiber devices, and cell foam. Such immobilization structures preferably are formed of materials including, for example, polystyrene, polypropylene, acrylate polymers, nylon, cloth, nitrocellulose, agarose, sepharose, and so forth.

According to this method of the invention, the hematopoietic cells in an immobilization structure or in an alternative cell culturing device containing soluble DPIV inhibitor are contacted with a sufficient amount of an inhibitor of DPIV to increase the number of hematopoietic cells and/or to cause the differentiation of such cells when the cells are cultured in the presence of the inhibitor. In general, the determination of an increase in the number of hematopoietic cells and/or their state of differentiation is assessed using conventional methods known to those of ordinary skill in the art. An important advantage of the present invention is that the cultured hematopoietic cells can be caused to differentiate and/or increase in number in the absence of exogenously added cytokines. By providing a method for stimulating hematopoietic cells in the absence of exogenously added cytokines, the invention provides substantial cost savings to the culturing of such cells, as well as advantageously reducing the likelihood of contamination of such cell cultures by eliminating what applicants have discovered is no longer an essential agent for stimulating hematopoietic cells in culture.

According to another aspect of the invention, an apparatus is provided for practicing the methods of the invention. The apparatus includes a container and an inhibitor of DPIV contained therein or attached thereto. Preferably, the container is a sterile container which is selected from any of the foregoing cell culture containers known to those of ordinary skill in the art. The inhibitor of DPIV is contained in the container in soluble or immobilized form or directly attached to the internal surface of the container. For example, the inhibitor of DPIV can include magnetic particles to which are attached one or more different inhibitors of DPIV. In addition to containing the immobilized or soluble DPIV inhibitor, the container optionally includes one or more growth media components for cell culture. Such components are known to those of ordinary skill in the art.

According to yet another aspect of the invention, a kit for stimulating hematopoietic cells in culture is provided. The kit contains the apparatus described above and instructions for using the apparatus to stimulate hematopoietic cells in vitro.

According to still another aspect of the invention, a method for stimulating hematopoietic cells and expanding antigen-specific T cells in vitro is provided. The stimulating and expansion steps can be performed concurrently or sequentially. Three embodiments of this method are described below to illustrate this method. In general, the embodiments differ from one another in the selection of the hematopoietic cells that are stimulated in vitro. In each embodiment, the culturing step(s) can be performed in the presence or absence of added cytokines or stromal cells. The preferred heteroconjugates that are used in each embodiment contain a tumor-specific antigen or a pathogen-specific antigen conjugated to a DPIV inhibitor of the invention.

The first embodiment of the method for obtaining antigen-specific T cells involves stimulating bone marrow cells in culture. The bone marrow cells in culture may include a mixture of cells; however, preferably, the bone marrow cells in culture are isolated CD34+ cells or isolated stem cells. According to this embodiment, the method involves: (1) culturing the bone marrow cells in the presence of a sufficient amount of a DPIV inhibitor (e.g., a DPIV monomer and/or homoconjugate) to expand the number of early T lineage cells in culture; and (2) culturing the early T lineage cells with a sufficient amount of a heteroconjugate containing an inhibitor of a DPIV inhibitor attached to an antigenic peptide (e.g., a tumor- or pathogen-specific antigen) to expand the number of antigen-specific T cells in the culture. Step (2) can be performed in the presence or absence of specific antigen. Steps (1) and (2) can be performed concurrently or sequentially. In general, the number of antigen-specific T cells is compared to a control culture of bone marrow cells that is treated as described in steps (1) and (2) with the exception that the control culture is not contacted with the heteroconjugate. At each step, the cells are cultured in the presence of the DPIV inhibitor or heteroconjugate for a time sufficient to increase the number of early T lineage cells and to expand the number of antigen-specific T cells, respectively, relative to the numbers of such cells that are present in the control culture.

The second embodiment is directed to stimulating umbilical cord blood cells in culture. This embodiment involves: (1) culturing the umbilical cord blood cells in the presence of a sufficient amount of a DPIV inhibitor (e.g., a DPIV monomer and/or homoconjugate) to expand the number of early T lineage cells in culture; and (2) culturing the early T lineage cells with a heteroconjugate containing an inhibitor of a DPIV inhibitor attached to an antigenic peptide (e.g., a tumor- or pathogen-specific antigen) to expand the number of antigen-specific T cells that are present in the culture. Step (2) can be performed in the presence or absence of the specific antigen. Steps (1) and (2) can be performed concurrently or sequentially. In general, the number of antigen-specific T cells is compared to a control culture of umbilical cord blood cells that is treated as described in steps (1) and (2) with the exception that the control culture is not contacted with the heteroconjugate. At each step, the cells are cultured in the presence of the DPIV inhibitor or heteroconjugate for a time sufficient to increase the number of early T lineage cells and to expand the number of antigen-specific T cells, respectively, relative to the numbers of such cells that are present in the control culture.

The third embodiment is directed to stimulating peripheral blood stem cells in culture. This embodiment involves: (1) culturing the peripheral blood stem cells in the presence of a sufficient amount of a DPIV inhibitor (e.g., a DPIV monomer and/or homoconjugate) to expand the number of T cells in culture; and (2) culturing the T cells with a sufficient amount of a heteroconjugate containing an inhibitor of a DPIV inhibitor attached to an antigenic peptide (e.g., a tumor- or pathogen-specific antigen) to expand the number of antigen-specific T cells in the culture. Step (2) can be performed in the presence or absence of the specific antigen. Steps (1) and (2) can be performed concurrently or sequentially. In general, the number of antigen-specific T cells is compared to a control culture of peripheral blood stem cells that is treated as described in steps (1) and (2) with the exception that the control culture is not contacted with the heteroconjugate. At each step, the cells are cultured in the presence of the DPIV inhibitor or heteroconjugate for a time sufficient to increase the number of T cells and to expand the number of antigen-specific T cells, respectively, relative to the numbers of such cells that are present in the control culture. Alternatively, because peripheral blood is known to contain T cells, it is possible to expand the number of antigen-specific T cells in culture without the stimulation step (1), i.e., the method for expanding the number of antigen-specific T cells involves culturing the peripheral blood cells with a sufficient amount of a heteroconjugate containing an inhibitor of a DPIV inhibitor attached to an antigenic peptide (e.g., a tumor- or pathogen-specific antigen) to expand the number of antigen-specific T cells in the culture. This step can be performed in the presence or absence of the specific antigen.

These and other aspects of the invention, as well as various advantages in utilities will be more apparent with reference to the drawings and detailed description of the invention.

A: Bulk Umbilical Cord Blood; Total Cell Counts. Control culture: $0.2\times10^6$ cells; Growth factors $5\times10^6$ cells; Val-boroPro: $3\times10^6$ ($10^{-6}$M); $3\times10^6$ ($10^{-8}$M); $4\times10^6$ ($10^{-10}$M).

B: CD34+ isolated cells: CD34+ cells were isolated using CD34mAb coupled beads for positive selection. Cell preparation contained 98% CD34+ cells. After 4 days of incubation the culture containing $10^{-10}$M Val-boroPro contained $8.5\times10^6$ cells, compared to $0.6\times10^6$ cells in the control and $4\times10^6$ cells in the incubation with growth factors.

C: The total number of cells in the combined culture increased to $55\times10^6$ cells as compared to $8.5\times10^6$ cells in the incubation with Val-boroPro alone.

D: Percent of CD34+ cells remaining after 4 day culture: Cultures incubated with Val-boroPro contained between 10 and 15% of CD34+ cells after 4 day culture. Cultures incubated with Growth Factors had only 4% of CD34+ cells remaining. This indicated that Val-boroPro has a growth stimulatory effect on CD34+ cells in addition to an effect on the differentiation of CD34+ cells into mature peripheral blood cells. This is supported by the observation that culturing these CD34+ cells in the presence of Val-boroPro and growth factors does not change the % CD34+ cells in the culture from the percentage seen with Val-boroPro alone.

Figure 3:
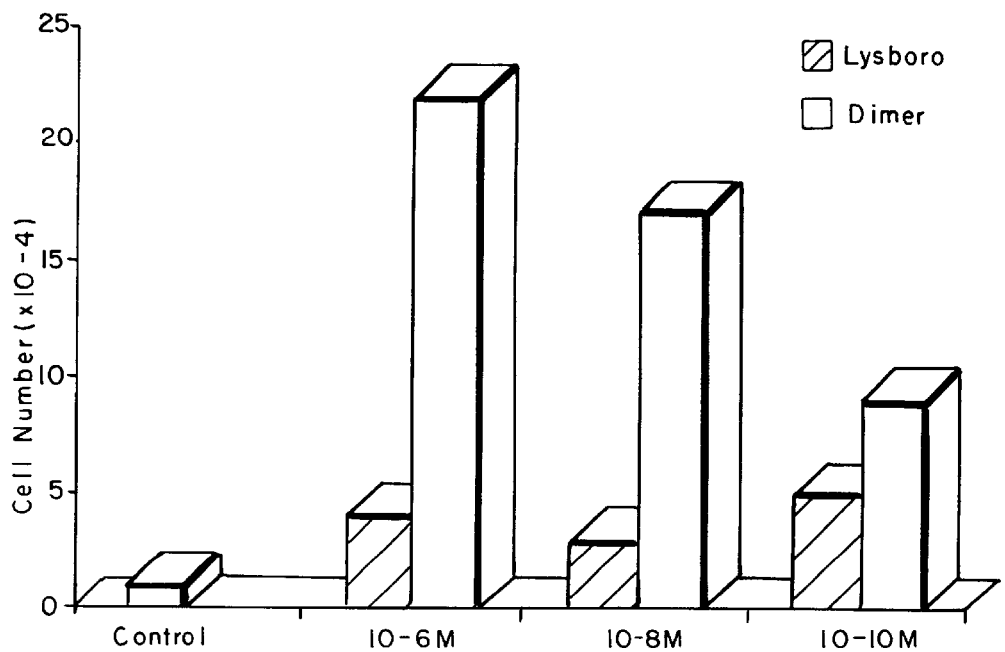
Figure 2D:
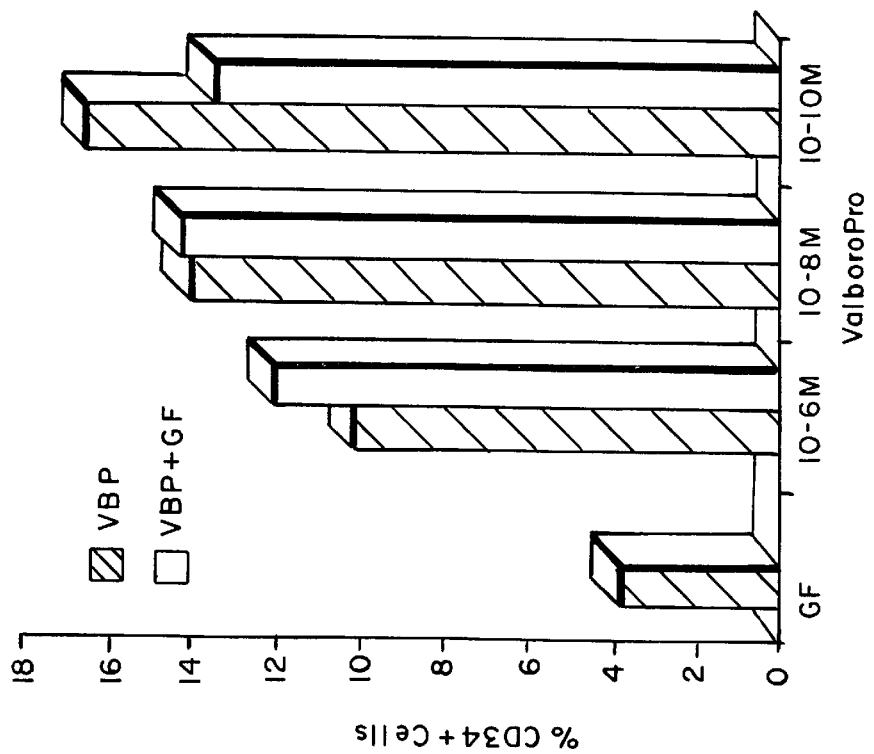
Figure 2C:
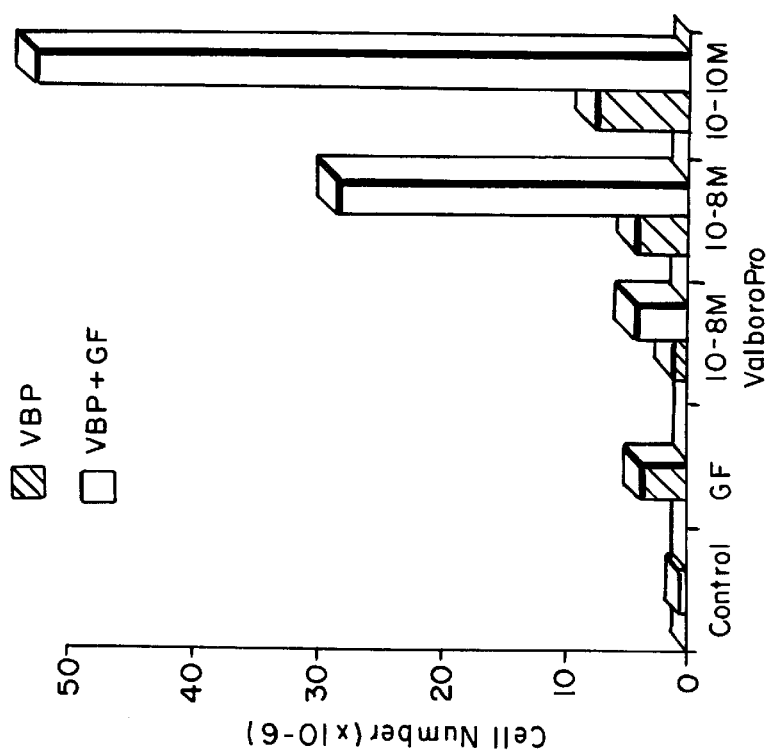

FIG. 3: Dimerization of Lys-boroPro (homoconjugate) dramatically increases the stimulation of bone marrow cell growth when compared to the effect of the monomeric form of Lys-boroPro. Cultures were set up as described in the legend to FIG. 1 except that Lys-boroPro and the homoconjugate were used, and incubated for 4 days.

Figure 1:
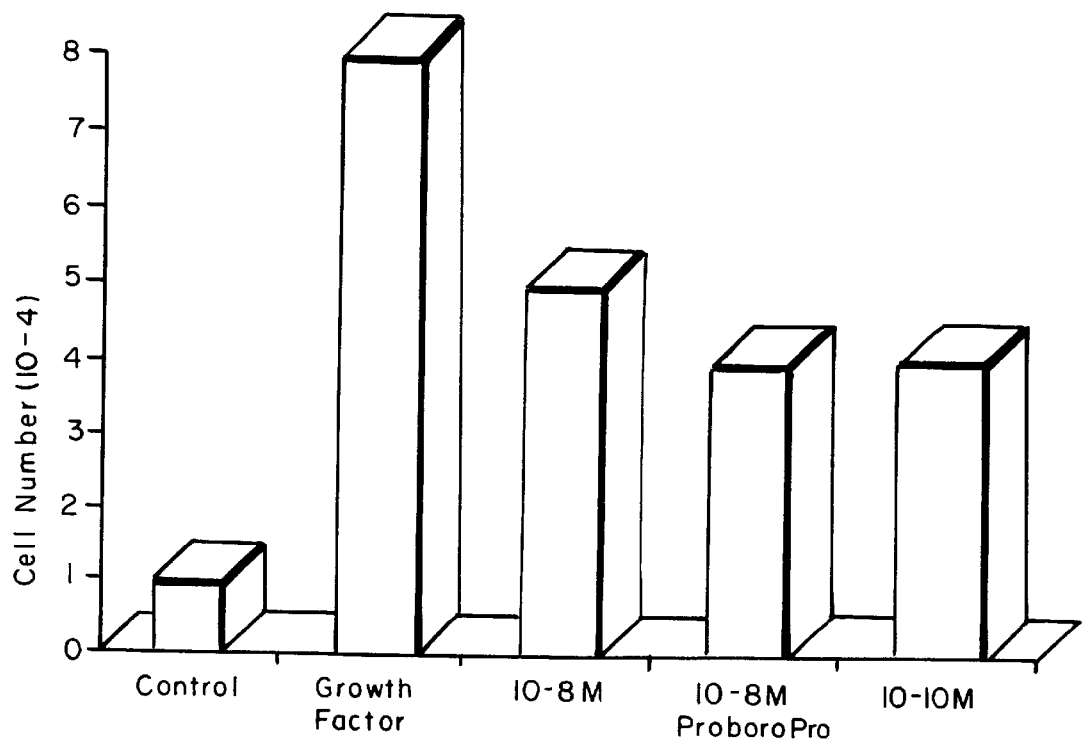
FIG. 1: Freshly isolated bone marrow cells were isolated and 10,000 cells per well were incubated in 96 microtiter plates in CellGro Iscove's Modified Dulbecco's Medium (IMDM) and with or without (control) the indicated concentrations of Pro-boroPro for 4 days. At the end of this incubation period, the cells were counted under the microscope. The cultures without Pro-boroPro contained 10,000 cells at the end of 4 days. The cultures containing Pro-boroPro had 53,000 cells at $10^{-6}$M, 38,000 cells at $10^{-8}$M and 42,000 cells at $10^{-10}$M. The cultures containing a growth factor mix (GF) contained 82,000 cells. Growth factors were supplied in OPITEN® Giant Cell Tumor-conditioned medium (IGEN)
Figure 2A:
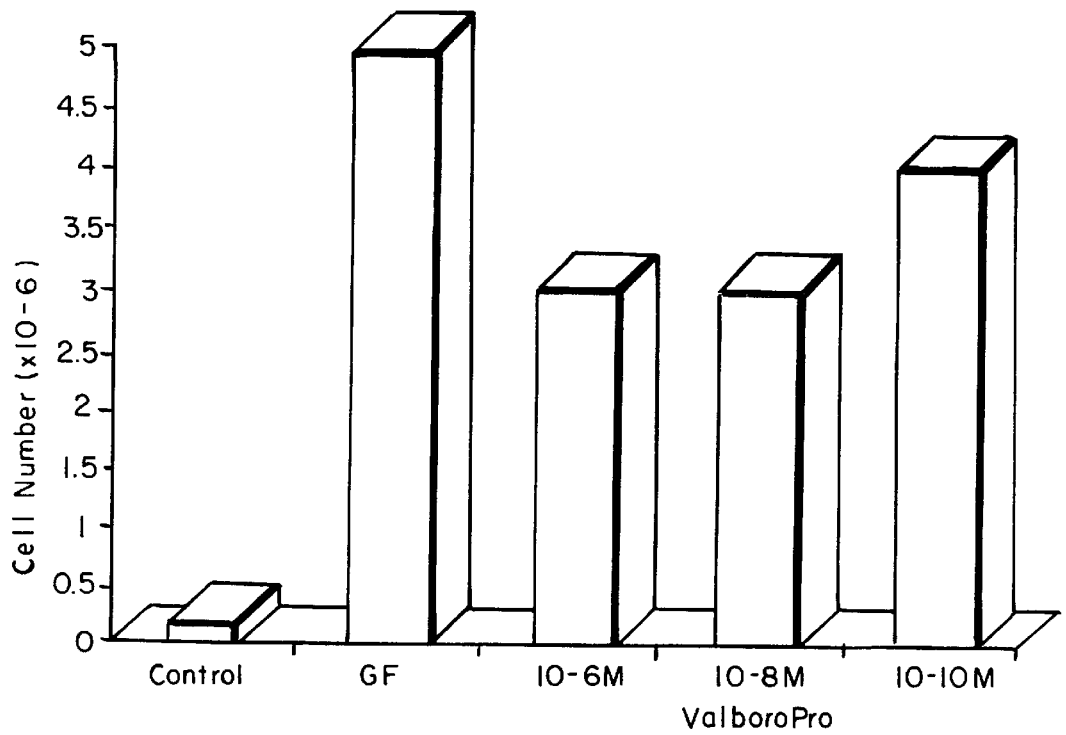
FIG. 2 Umbilical cord blood cells were incubated under essentially the same conditions as described in the legend to FIG. 1, except that Val-boroPro was used as stimulant at the indicated concentrations. After 4 day incubation.
Figure 2B:
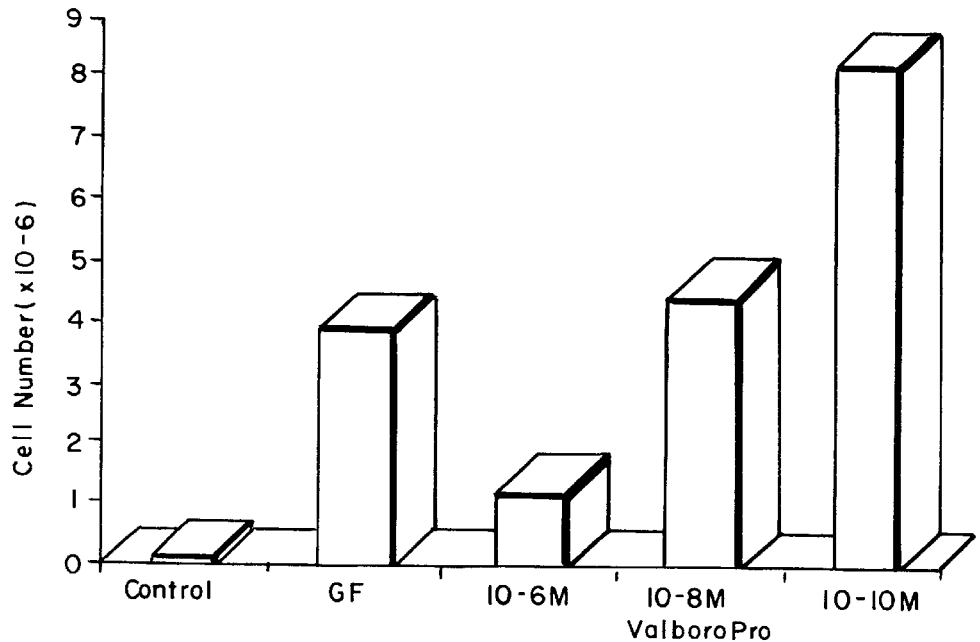
Figure 4A:
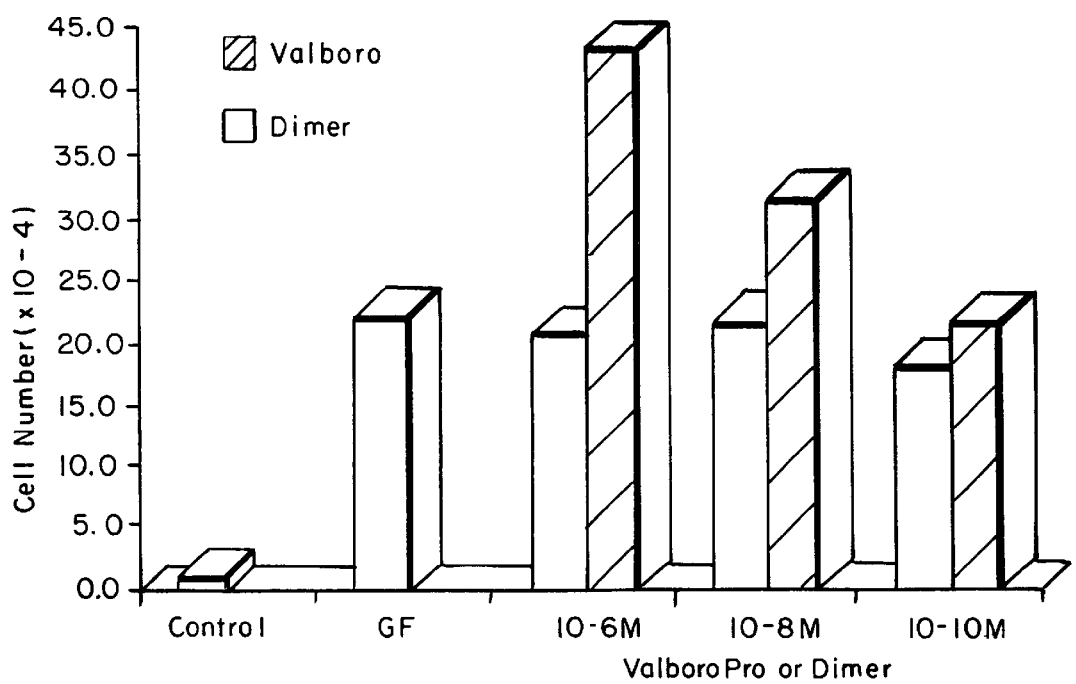
Figure 4C:
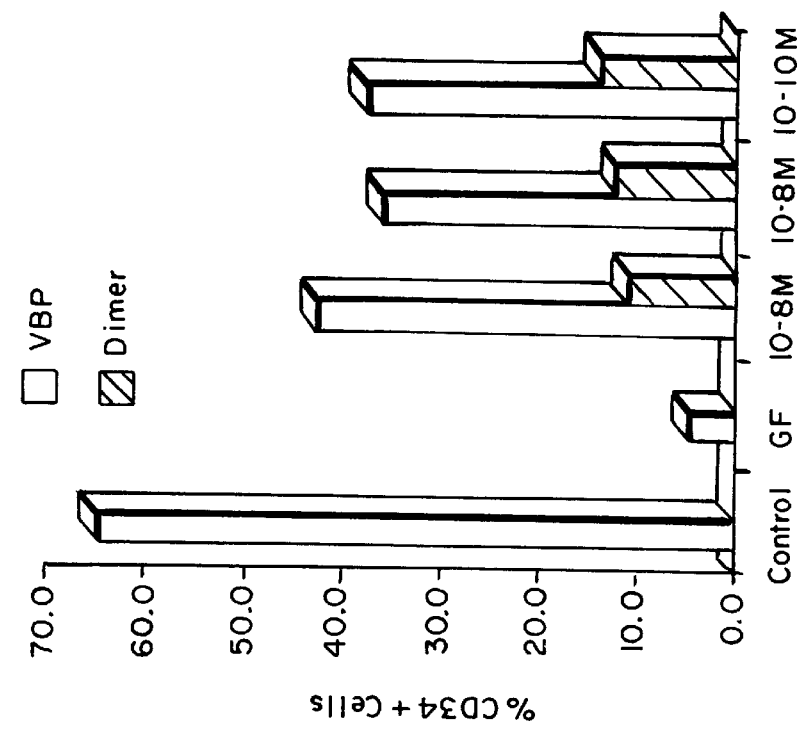
Figure 4B:
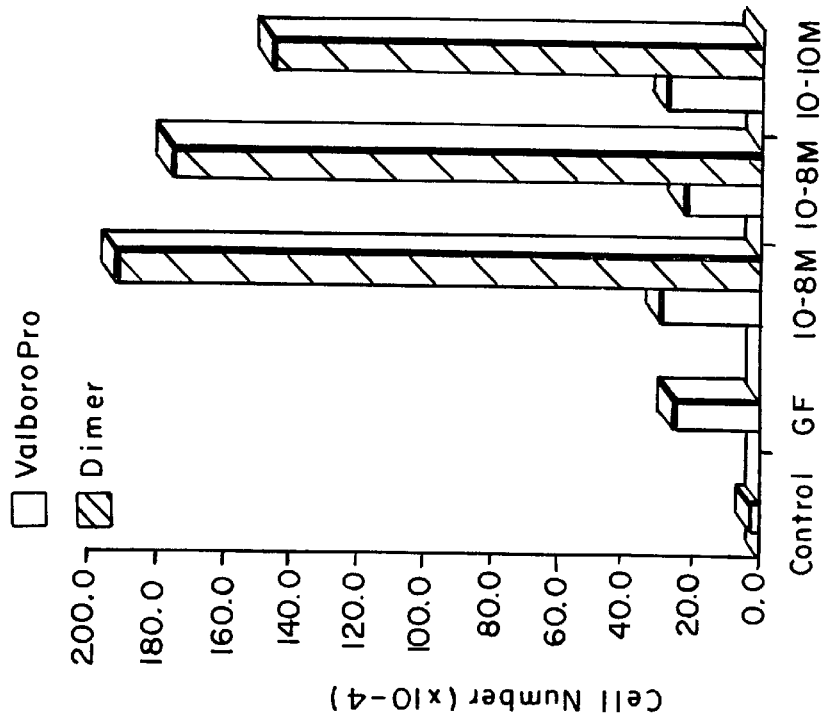

FIG. 4 Bone marrow cells were incubated as described in FIG. 1 except that Val-boroPro and the homoconjugate were used in a 4 day culture.

A: Val-boroPro gave a similar expansion of bone marrow cells as the growth factor mix (GF), while the dimer more than doubled the effect.

B: (panel a): Isolated CD34+ cells (98% purity) incubated with Val-boroPro gave up to 20 fold increase in stimulation of cellular growth compared to an 18 fold increase with growth factors over that in control cultures. The homoconjugate increased growth activity by 125 fold at a concentration of $10^{-6}$M and 96 fold at $10^{-6}$M.

C: Percent of CD34+ cells remaining in culture after a 4 day incubation period: control 63%; GF 5%; Val-boroPro 43%; homodimer 10%.

DETAILED DESCRIPTION OF THE INVENTION

The present invention provides an improved method for stimulating hematopoietic cells in culture and, in particular, a method for stimulating hematopoietic cells in vitro in the absence of exogenously added cytokines. Applicants' invention relates to the discovery that the addition of cytokines or cytokine-expressing cells (stromal cells) to hematopoietic cells in culture is not an essential element for hematopoietic cells maintenance or stimulation when a DPIV inhibitor is added. Accordingly, Applicants' discovery results in significant cost savings by eliminating the need to provide cytokines to cell cultures, as well as advantageously eliminating a potential source of contamination to such cells in culture.

According to one aspect of the invention, a method for stimulating hematopoietic cells in vitro is provided. The method involves (1) contacting the hematopoietic cells with a sufficient amount of an inhibitor of a dipeptidyl peptidase type IV ("DPIV") in vitro to increase the number of hematopoietic cells and/or the differentiation of such hematopoietic cells relative to the number and differentiation of hematopoietic cells that are present in a control culture that is not contacted with the inhibitor but is otherwise subjected to the same culture conditions as the hematopoietic cells which are cultured in the presence of the inhibitor; and (2) culturing the hematopoietic cells in the presence of the inhibitor and in the absence of exogenously added cytokines under conditions and for a time sufficient to increase the number of hematopoietic cells and/or their differentiation relative to the number of hematopoietic cells that were present in the control culture. Stimulating hematopoietic cells, as used herein, refers to inducing the hematopoietic cells to grow and/or differentiate. Thus, the methods and compositions and devices of the invention are useful for increasing the cell number as well as for causing differentiation of early progenitor cells.

Hematopoietic Cells

As used herein, hematopoietic cells refer to cells which are related to the production of blood cells. Exemplary hematopoietic cells include hematopoietic stem cells, primordial stem cells, early progenitor cells, CD34+ cells, early lineage cells of the mesenchymal, myeloid, lymphoid and erythroid lineages, bone marrow cells, blood cells, umbilical cord blood cells, stromal cells, and other hematopoietic precursor cells that are known to those of ordinary skill in the art.

In accordance with the convention in art, the definition of hematopoietic cells excludes thymocytes. Thymocytes from the thymus are not considered "hematopoietic progenitor" cells since such cells are obtained from the thymus and are already committed. Applicants have discovered that certain methods of the invention are useful in connection with hematopoietic cells, as well as with thymocytes. Accordingly, it is to be understood that the methods of the invention can be practiced with hematopoietic cells alone, thymocytes alone, or hematopoietic cells in combination with thymocytes.

Bone marrow cells contain totipotent stem cells which give rise to hematopoietic cells of all lineages including the lymphoid, myeloid and erythroid lineages. Stem cells have the ability to renew themselves as well as to differentiate into progenitor cells of all hematopoietic lineages. Progenitor cells retain the ability to proliferate and give rise to differentiated cells of all lineages. Differentiated cells lose the ability to proliferate and exhibit morphological characteristics specific for their lineages (such as macrophages, granulocytes, platelets, red blood cells, T cells and B cells). Bone marrow includes stem cells as well as progenitor cells of the lymphoid (T and B cells), myeloid (e.g., granulocytes, macrophages) and erythroid (red blood cells) lineages. Stem cells and progenitor cells express CD34 on their surface while differentiated cells do not. Accordingly, the detection of CD34 can be used to distinguish differentiated from undifferentiated cells.

For use in bone marrow transplants, hematopoietic precursor cells can be derived either from the cancer patient (autologous transplant) or from a histocompatible donor (allogeneic donor). These cells can be isolated from bone marrow, peripheral blood or from umbilical cord blood. In general, the cells are harvested before chemotherapy or radiation therapy. Bone marrow typically is aspirated from the iliac crest and is a lengthy and painful procedure. Bone marrow is rich in CD34+ cells; typically 1 to 2% of marrow cells are precursor cells. Peripheral blood typically contains less than 1% CD34+ cells. To enrich for CD34+ cells, blood progenitor cell are mobilized from bone marrow into the periphery by pretreatment with low dose of chemotherapy or with certain cytokines such as G-CSF or SCF. Umbilical cord blood is very rich in early progenitor cells and shows great promise as a source of cells for hematopoietic cell transplant.

The number of progenitor cells that can be harvested at one time from either source is small and, in many cases, is not sufficient for a successful transplant. Several methods have been developed to expand bone marrow cells or progenitor cells obtained from blood aphereses or from umbilical cord blood in in vitro cultures. The ability to expand these cells has helped advance bone marrow transplant technology as a viable adjunct therapy for cancer treatments that involve high dose chemotherapy and/or irradiation. In vitro expansion of hematopoietic stem cells requires the addition of appropriate growth factors as well as certain growth conditions provided by so called stromal cells. Stromal cells provide physical support to hematopoietic progenitor cells as well as certain growth factors required for the increase of stem cell numbers.

Separation of CD34+ cells (differentiated cells) from undifferentiated cells can be achieved by a number of different methods. The most widely used is a positive immunological selection based on binding of these cells to anti-CD34-antibodies immobilized on a solid support (Cellpro, Baxter). Other selection methods include negative selection where all cells not expressing CD34 are isolated away from the CD34+ cells based on their expression of lineage specific cell surface antigens.

In certain embodiments of the invention, hematopoietic cells are stimulated with the monomers in the absence of added cytokines, stromal cells or thymocytes. In other embodiments, hematopoietic cells or thymocytes are stimulated with the compounds of the invention (preferably, excluding monomers) in the absence or presence of added cytokines or stromal cells. Applicants have used representative monomers and conjugates of the invention to stimulate isolated CD34+ cells (e.g., stromal cells have been removed) in the absence of added cytokines and/or stromal cells. Applicants also have demonstrated that such cells can be stimulated to grow and differentiate in liquid culture. Thus, one important advantage of the present invention is that the methods disclosed herein do not require stromal cells for hematopoietic cell or thymocyte stimulation. Another important advantage of the invention is that the compounds and methods disclosed herein are useful for stimulating human stem cells (CD34+). Such target cells are important targets for expansion because of their ability to differentiate into mature cell types that have important therapeutic applications. The stimulation of stem cells in the absence of added cytokines or stromal cells previously has not been reported.

Culturing the Hematopoietic Cells

Expansion of progenitor cells can be carried out in a variety of different culture vessels and under different culture conditions. In general, the same culturing conditions that are used for culturing hematopoietic cells using the prior art methods are used herein, with the exception that the DPIV inhibitors are substituted for the cytokines in the prior art culture methods. An exemplary prior art protocol for culturing cells is provided below. Accordingly, this protocol is modified for use in accordance with the methods of the invention by culturing the cells in the presence of DPIV inhibitors and in the absence of exogenously added cytokines.

Following separation, precursor cells are incubated in culture medium such as RPMI, Iscove's DMEM, TC 199, X-VIVO-10, preferably with addition of human or fetal calf serum and a mixture of growth factors. Serum or plasma can be added at a concentration of 5 to 50%. Growth factors include any or all Interleukins (IL-1 to IL-16), interferons (INF-alpha, beta and gamma), erythropoietin (EPO), stem cell factor (SCF), insulin like growth factors, fibroblast growth factors, platelet-derived growth factor, tumor growth factor beta, tumor necrosis factor alpha, granulocyte colony stimulating factor (G-CSF), granulocyte-macrophage colony stimulating factor (GM-CSF), macrophage colony stimulating factor (M-CSF), fins-like tyrosine kinase-3 ligand (Fft-3 ligand), and cKIT ligand (cKL). Many of these growth factors are commercially available. Most commonly used mixture of growth factors includes G-CSF, GM-CSF, SCF, IL-1, IL-3 and IL-6. Most of the growth factors used are produced by recombinant DNA techniques are purified to various degrees. Some growth factors are purified from culture media of tumor cell lines by standard biochemical techniques. A widely used growth factor is PIXY 321 which is produced by recombinant technology and exhibits both, GM-CSF and IL-3 activity. The amount of growth factors used in the cultures depends on the activity of the factor preparation and on the combination of growth factors used. Typically, concentrations range from 0.5 to 500 ng/ml. The optimum concentration of each growth factor has to be determined for individual culture conditions since some growth factors act synergistically with other growth factors. As noted above, the methods of the invention exclude exogenously added cytokines and, instead, utilize DPIV inhibitors to stimulate the hematopoietic cells in culture.

Increasing the number of hematopoietic cells, as used herein, means increasing the number of cells by at least approximately 2-fold relative to the number of hematopoietic cells that are present in a parallel control culture of cells that are subjected to the same conditions as the DPIV inhibitor-treated cultures with the exception that such control cultures are not contacted with the DPIV inhibitors. Preferably, the number of hematopoietic cells are increased at least approximately 4-fold, more preferably, 10-fold and, most preferably, at least 20-fold relative to the number of hematopoietic cells that are present in the parallel control culture.

The time period in which the number of hematopoietic cells are increased is, at least in part, a function of the cell type and on the specific culture vessel used. In general, this time period ranges from about 2–3 days (for short term expansion) to several weeks for the expansion of cells suitable for long term engraftment. Routine procedures known to those of ordinary skill in the art can be used to determine the number of cells in culture as a function of increasing incubation time of the cultured cells with the DPIV inhibitor. Typically, expansion (increase in cell number) is measured by counting the cell numbers by, for example, measuring incorporation of a specific dye or determining the hematocrit, using a hematocytometer or cell counter. Thus, the optimization of the particular growth conditions and selection of the amounts of DPIV inhibitors that are necessary to achieve the above-noted fold increases in cell numbers are determined using no more than routine experimentation. Such routine experimentation involves, for example, (i) varying the amount of the DPIV inhibitor at constant incubation time; (ii) varying the incubation time at constant amounts of DPIV inhibitor; (iii) applying the foregoing optimization experiments to determine the particular conditions necessary to achieve a pre-selected fold increase in cell number for a pre-selected cell type; and (iv) varying other factors including, for example, the identity, valency (e.g., monovalent or bivalent), or the state of the DPIV inhibitor (whether soluble or immobilized), to optimize the culture conditions to achieve the desired results. Thus, the length of cell culture incubation period varies and depends on the degree of desired expansion. For most applications, this period ranges from about 4 to 14 days. In general, expansion in liquid cultures is evaluated by the increase in total number of cells from the start of incubation and/or by determining the % CD34+ cells in the culture and/or by determining the increase in total cells relative to a control culture that has not been contacted with the DPIV inhibitor. CFU-GM number is evaluated when cells are inoculated in Iscove's methylcellulose medium, containing appropriate growth factors, in 35 mm petri dishes for 10 to 14 days. The typical starting density is 1000 cells/ml. At the end of the incubation period, number of colonies containing more than 50 cells of myeloid (CFU-GM) or erythroid (BFU-E) origin is scored using an inverted microscope.

After expansion, the cells are harvested and washed with fresh culture medium before infusion to the patient.

Contacting the Hematopoietic Cells with the DPIV Inhibitors

As used herein, contacting the hematopoietic cells with the DPIV inhibitor means introducing the DPIV inhibitors to the cultures in a manner which permits the DPIV inhibitors to be in direct physical contact with the cells. In general, the soluble DPIV inhibitors are contacted with the cells in culture in the same manner in which soluble cytokines or other soluble growth factors are introduced into cell cultures, with the exception that the soluble DPIV inhibitors are substituted for the more conventional cytokine factors of the prior art. Thus, for example, the soluble DPIV inhibitors can be added as an aqueous solution to the cell culture or in powder (e.g., lyophilized) form to result in an aqueous solution in the cell culture matrix. An exemplary procedure for contacting several representative DPIV inhibitors is provided in the Examples.

In general, the insoluble DPIV inhibitors are contacted with the cells in culture in a manner which is dictated by the physical form of the insoluble DPIV inhibitors. An insoluble DPIV inhibitor refers to a DPIV inhibitor that is not and cannot be placed in solution. Accordingly, insoluble DPIV inhibitors refer to DPIV inhibitors that are attached to an insoluble support. The insoluble support can be a cell culture vessel, in which instance the inhibitors are attached to the culture-contacting surface of the culture vessel or, alternatively, the insoluble support can be in particulate form (e.g., magnetic particles, sepharose), in which instance the inhibitors are attached to the surface of the particles. Accordingly, contacting insoluble DPIV inhibitors that are attached to the culture vessel surface involves placing the cells in the culture vessels, together with the appropriate nutrients that are known for hematopoietic cell growth but excluding exogenously added cytokines. Contacting insoluble DPIV inhibitors that are attached to particles involves introducing the particles (dry or suspended) to a culture vessel containing the hematopoietic cells. Alternatively, the hematopoietic cells can be added to a culture vessel which already contains the soluble or insoluble DPIV inhibitors. Regardless of the physical state of the DPIV inhibitors (soluble or insoluble), contacting the hematopoietic cells with the inhibitors is performed in the absence of exogenously added cytokines.

Introduction to DPIV Inhibitors

The DPIV inhibitors of the invention are molecules which bind to DPIV. In general, there are two categories of DPIV inhibitors: (1) active site inhibitors and (2) non-active site binding agents. Active site inhibitors refer to agents which bind to (covalently or via ionic interactions) the catalytic active site of DPIV and, thereby, inhibit the enzymatic activity of DPIV. Exemplary active site inhibitors include competitive enzymatic inhibitors of DPIV, such as transition state analogs of the natural DPIV substrates (described below). Non-active site binding agents refer to agents which bind to (covalently or via ionic interactions) a site on the DPIV protein other than the active site and which have the ability to stimulate hematopoietic cells or thymocytes under the conditions described herein. Binding of certain non-active site binding agents to DPIV (e.g., non-competitive DPIV inhibitors) alternatively can be detected by observing a reduction in DPIV enzymatic activity following exposure to the non-active site binding agent. Exemplary non-active site binding agents include antibodies to DPIV and fragments thereof which selectively bind to DPIV in a manner that results in the ability of the binding agent to stimulate hematopoietic cells and/or thymocytes when cultured with such cells under the conditions described herein.

Assays to measure DPIV enzymatic activity have been described (W. G. Gutheil and W. W. Bachovchin, *Biochemistry* 32, 8723–8731 (1993); Gutheil, W. G., and W., B. W. Kinlsq, *Analytical Biochemistry* 223, 13–20 (1994); and Gutheil, W. G., et al., *Proc. Natl. Acad. Sci. U.S.A.* 91, 6594–6598 (1994)). These methods use the chromatogenic substrate Ala-Pro-p-nitroanilide (AppNA) and fluorescent substrate Ala-Pro-7-amino-4-trifluoromethyl coumarin (AP-AFC). AppNA and AP-AFC are commercially available (e.g., Enzyme Systems Products, Dublin, Calif.). Such methods can be used as screening assays to determine whether a DPIV inhibitor inhibits the enzymatic function of DPIV in vitro.

DPIV Inhibitors That Bind to the Active-Site of DPIV

DPIV is a member of the serine protease family which exhibits a postprolyl cleavage activity. Accordingly, the natural substrate of DPIV is a peptide which contains, at its amino terminus, the dipeptide Xaa-Pro, where Xaa represents any amino acid and Pro represents proline in accordance with standard amino acid nomenclature. The active-site inhibitors of the invention inhibit the binding and/or cleavage reaction by DPIV of its natural substrate.

Monomeric active-site binding inhibitors of the invention are represented by the formula I:

$$\text{Surface-(L)}_q\text{-P}^1\text{R}^1 \qquad (I)$$

wherein $P^1$ represents a first targeting moiety, preferably a peptide, that mimics the substrate binding site of DPIV;

$R^1$ represents a reactive group that reacts with a functional group in the reactive center of DPIV;

L represents an optionally present linker molecule (i) having a molecular weight ranging from about 100 daltons to about 2000 daltons, (ii) having a length ranging from about 20A to about 300 A; (iii) containing a chain of atoms selected from the group consisting of C, O, N, S, and phosphorus atoms, connected by single, double or triple bonds; and, (iv) if attached to a surface, having a surface density ranging from about 20A to about 300 A, i.e., the distance between one covalent attachment of the linker molecule to the surface and the next covalent attachment of the linker molecule to the surface; and q is 0 or 1, i.e., when q=0, the linker is absent and the monomeric active-site binding inhibitor is not attached via the linker to a surface (e.g., tissue culture vessel surface or magnetic particle) and when q=1, the linker is present and the monomeric active-site inhibitor is attached via the linker to a surface. In such embodiments, L is referred to as a bivalent linker because it serves to covalently couple a single binding moiety to a surface. Such bivalent linkers are known to those of ordinary skill in the art and are described in more detail below.

Peptides $P^1$ that mimic the substrate binding site of DPIV include competitive inhibitors of DPIV, such as transition state analogs of DPIV and non-competitive inhibitors of DPIV, such as fluoroalkylketones. Each of these types of inhibitors is discussed below. In important embodiments of the invention, $P^1$ is a peptide or a peptidomimetic.

Multivalent active-site inhibitors of the invention are represented by the formula II:

$$[P^2(R^2)_m]_n \text{——} (L)_q \text{——} P^1R^1] \atop \phantom{xxxxxxxxxx} | \atop \phantom{xxxxxxxxxx} (A)_r \atop \phantom{xxxxxxxxxx} | \atop \phantom{xxxxxxxx} \text{Surface}$$

$$(II)$$

where $P^1$, $R^1$, L are defined above and q=1;

$P^2$ represents a second targeting moiety, preferably a peptide, that may be the same or different from the first targeting moiety;

$R^2$ represents a second reactive group that may be the same or different from the first reactive group;

m=0 or 1;

n is a whole number from 0 to 10;

r=0 or 1; and

A is an arm of the linker which can be coupled to a surface, i.e., when r=0, the linker, L, is not coupled to a surface and when r=1, the linker is coupled to a surface.

In certain embodiments of the invention, if $P^2=P^1$, then $R^2$ can be absent, the same, or different from $R^1$. In general, n is 1 and the compounds of the invention are referred to as homoconjugates (i.e., $P^2=P^1$) or heteroconjugates (i.e., $P^2 \neq P^1$).

In certain embodiments, L is further attached via a surface (e.g., a tissue culture vessel or magnetic particle). In such embodiments, L is referred to as a multivalent linker because it serves to covalently couple two or more binding moieties to one another as well as to a surface. Such multivalent linkers are known to those of ordinary skill in the art.

Exemplary binding moieties $R^1$ that are peptides and that reportedly have utility for inhibiting post-prolyl cleaving enzymes and which, if coupled to a reactive group, form a covalent complex with a functional group in the reactive site of a post-prolyl cleaving enzyme are described in U.S. Pat. No. 4,935,493, "Protease Inhibitors", issued to Bachovchin et al. ("Bachovchin '493"); U.S. Pat. No. 5,462,928, "Inhibitors of Dipeptidyl-aminopeptidase Type IV", issued to Bachovchin et al. ("Bachovchin '928"); U.S. Pat. No. 5,543,396, "Proline Phosphonate Derivatives", issued to Powers et al., ("Powers '396"); U.S. Pat. No. 5,296,604, "Proline Derivatives and Compositions for Their Use as Inhibitors of HIV Protease", issued to Hanko et al., ("Hanko '604"); PCT/US92/09845, "Method for Making a Prolineboronate Ester", and its U.S. priority applications (U.S. Ser. Nos. 07/796,148 and 07/936,198), Applicant Boehringer Ingelheim Pharmaceuticals, Inc. ("Boehringer"); and PCT/GB94/02615, "DPIV-Serine Protease Inhibitors", Applicant Ferring V. V. ("Ferring"). Representative examples of the foregoing inhibitors are described below and include the transition-state analog-based inhibitors Xaa-boroPro, include Lys-BoroPro, Pro-BoroPro and Ala-BoroPro in which "boroPro" refers to the analog of proline in which the carboxylate group (COOH) is replaced with a boronyl group $[B(OH)_2]$. Alternative active-site inhibitors of the invention have an analogous structure in which the boronyl group is replaced by a phosphonate or a fluoroalkylketone (described below). Those skilled in the art will recognize that there are other such changes which can be made without significantly affecting the binding and complex forming character of these compounds.

The development of phage display libraries and chemical combinatorial libraries from which synthetic compounds can be selected which mimic the substrate binding site of DPIV permits the identification of further $P^1$ targeting moieties to which an $R^1$ reactive group can be covalently attached to form a binding moiety which mimics the substrate binding site of the protease and which forms a complex with a functional group in the protease reactive site. Such libraries can be screened to identify non-naturally occurring putative targeting moieties by assaying protease cleavage activity in the presence and absence of the putative phage display library molecule or combinatorial library molecule and determining whether the molecule inhibits cleavage by the protease of its natural substrate or of a substrate analog (e.g., a chromophoric substrate analog which is easily detectable in a spectrophotometric assay). Those phage library and/or combinatorial library molecules which exhibit inhibition of the protease then can be covalently coupled to the reactive groups $R^1$ disclosed herein and again tested to determine whether these novel molecules selectively bind to the protease (e.g., by repeating the above-noted screening assay). In this manner, a simple, high-through-put screening assay is provided for identifying non-naturally occurring targeting moieties of the invention.

In general, the first binding moieties, $P^1$, of the invention are covalently coupled via a carboxyl group at their carboxyl terminal amino acid to a first reactive group, $R^1$. As used herein, $R^1$ refers to a reactive group that is capable of reacting with a functional group in a reactive center of DPIV. By reacting with a reactive center of this target protease, it is meant that the $R^1$ forms a covalent bond or a strong ionic interaction with a functional group that is located in the active site. $R^1$ reactive groups that are embraced within the invention include the reactive groups referred to as group "T" in U.S. Pat. No. 4,935,493, "Protease Inhibitors", issued to Bachovchin, et al. These include boronate groups, phosphonate groups, and fluoroalkylketone groups. Exemplary boronate groups are described below and in the Examples. The phosphonate and fluoroalkylketone groups are described below. In general, it is preferred that the linkage between the carboxyl terminus of the targeting moiety and the reactive group be in an L configuration. It also is preferred that the reactive group forms a covalent bond with a functional group in the active site; however, there is no requirement for covalent bond formation in order to form a complex between the binding moiety and the active site.

Throughout this application, conventional terminology is used to designate the isomers as described below and in appropriate text books known to those of ordinary skill in the art. (See, e.g., Principles in Biochemistry, editor A. L. Lehninger, page 99–100, Worth Publishers, Inc. (1982) New York, N.Y.; Organic Chemistry, Morrison and Boyd, 3rd Edition, Chap. 4, Allyn and Bacon, Inc., Boston, Mass. (1978); See also, Patent Cooperation Treaty published application WO93/10127, application no. PCT/US92/09845).

All amino acids, with the exception of glycine, contain an asymmetric or chiral carbon and may contain more than one chiral carbon atom. The asymmetric $\alpha$ carbon atom of the amino acid is referred to as a chiral center and can occur in two different isomeric forms. These forms are identical in all chemical and physical properties with one exception, the direction in which they can cause the rotation of plane-polarized light. These amino acids are referred to as being "optically active," i.e., the amino acids can rotate the plane-polarized light in one direction or the other.

The four different substituent groups attached to the $\alpha$ carbon can occupy two different arrangements in space. These arrangements are not super imposable mirror images of each other and are referred to as optical isomers, enantiomers, or stereo isomers. A solution of one stereo isomer of a given amino acid will rotate plane polarized light to the left and is called the levorotatory isomer [designated (−)]; the other stereo isomer for the amino acid will rotate plane polarized light to the same extent but to the right and is called dextrorotatory isomer [designated (+)].

A more systematic method for classifying and naming stereo isomers is the absolute configuration of the four different substituents in the tetrahedryin around the asymmetric carbon atom (e.g., the $\alpha$ carbon atom). To establish this system, a reference compound was selected (glyceraldehyde), which is the smallest sugar to have an asymmetric carbon atom. By convention in the art, the two stereo isomers of glyceraldehyde are designated L and D. Their absolute configurations have been established by x-ray analysis. The designations, L and D, also have been assigned to the amino acids by reference to the absolute configuration of glyceraldehyde. Thus, the stereo isomers of chiral compounds having a configuration related to that of L-glyceraldehyde are designed L, and the stereo isomers having a configuration related to D-glyceraldehyde are designated D, regardless of the direction in which they rotate the plane-polarized light. Thus, the symbols, L and D, refer to the absolute configuration of the four substituents around the chiral carbon.

In general, naturally occurring compounds which contain a chiral center are only in one stereo isomeric form, either D or L. The naturally occurring amino acids are the L stereo isomers; however, the invention embraces amino acids which can be in the D stereo isomer configuration.

Most amino acids that are found in proteins can be unambiguously named using the D L system. However, compounds which have two or more chiral centers may be in $2^n$ possible stereo isomer configurations, where n is the number of chiral centers. These stereo isomers sometimes are designated using the RS system to more clearly specify the configurations of amino acids that contain two or more chiral centers. For example, compounds such as threonine isoleucine contain two asymmetric carbon atoms and therefore have four stereo isomer configurations. The isomers of compounds having two chiral centers are known as diastereomers. A complete discussion of the R S system of designating optical isomers for amino acids is provided in Principles in Biochemistry, editor A. L. Lehninger, page 99–100, supra. A brief summary of this system follows.

The R S system was invented to avoid ambiguities when a compound contains two or more chiral centers. In general, the system is designed to rank the four different substituent atoms around an asymmetric carbon atom in order of decreasing atomic number or in order of decreasing valance density when the smallest or lowest-rank group is pointing directly away from the viewer. The different rankings are well known in the art and are described on page 99 of Lehninger. If the decreasing rank order is seen to be clockwise, the configuration around the chiral center is referred to as R; if the decreasing rank order is counter-clockwise, the configuration is referred to as S. Each chiral center is named accordingly using this system. Applying this system to threonine, one skilled in the art would determine that the designation, L-threonine, refers to (2S, 3R)-threonine in the RS system. The more traditional designations of L-, D-, L-allo, and D-allo, for threonine have been in common use for some time and continue to be used by those of skill in this art. However, the R S system increasingly is used to designate the amino acids, particularly those which contain more than one chiral center.

In a particularly preferred embodiment of the invention, the boroProline compound is a Val-boroProline compound. A "Val-boroProline compound" refers to a compound in which the carboxy terminal boroProline is covalently coupled via a peptide linkage in accordance with standard peptide chemistry to a valine amino acid residue. The valine amino acid, optionally, is further coupled via a peptide linkage to additional amino acid residues, provided that the additional amino acid residues do not inhibit the ability of the Val-boroProline compound to bind to CD26. In a most preferred embodiment, the compound of the invention is Val-boroPro (also referred to as "PT-100"). Because of the chiral carbon atoms present on the amino acid residues and on the carbon attached to the boron atom, Val-boroPro can exist in multiple isomeric forms: (a) L-Val-S-boroPro, (b) L-Val-R-boroPro, (c) D-Val-S-boroPro, and (d) D-Val-R-boroPro. More preferably, the compound is L-Val-S-boroPro or L-Val-R-boroPro. In an analogous manner, the other boroProline compounds of the invention can exist in multiple isomeric forms; however, in general, the forms in which each amino acid chiral center has an "L-" configuration and the boroPro is in the R or S configuration are the preferred forms of the compounds.

The first targeting moieties with a first reactive group $P^1R^1$ of the invention that are boroproline peptides can be considered as having the structure:

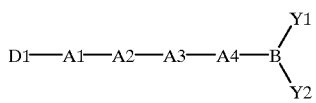

(a) wherein B is boron,
(b) wherein each of Y1 and Y2 is independently selected from the group consisting of a hydroxyl moiety and a reactive moiety that converts to a hydroxyl moiety under physiologic conditions,
(c) wherein -A3-A4- has the structure

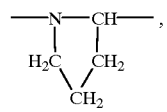

(d) wherein D1-A1-A2- is an amino acid having a structure selected from the the group consisting of:

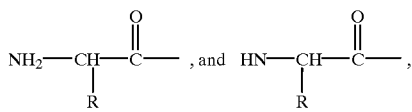

wherein R represents the side chain of the amino acid. These boroproline peptides are linked via amino peptide linkages and/or chemical crosslinking agents to the second targeting moiety, $P^2$, via the amino acid side chain R to, e.g., the side chain of an antigenic peptide, to form the above-described compounds, $[P^2(R^2)_m]_n\text{-}(L)_q\text{-}P^1R^1$. Exemplary peptides include an autoimmune disease antigenic peptide, an infectious disease antigenic peptide and an allergic disease antigenic peptide. The preferred antigenic peptides are peptides that bind to a T cell surface receptor or a B cell surface receptor, e.g., TCR/CD3, CD2, CD4, CD8, CD10, CD26, CD28, CD40, CD45, B7.1 and B7.2.

Alternatively, the reactive moiety can be a Fluoroalkylketone or a phosphonate group. The reactive groups of the invention that are fluoroalkylketone reactive groups have the formula:

where G is either H, F or an alkyl group containing 1 to about 20 carbon atoms and optional heteroatoms which can be N, S, or O. As used herein, the reactive groups of the invention that are phosphonate groups have the formula:

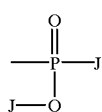

where each J, independently, is O-alkyl, N-alkyl, or alkyl (each containing about 1–20 carbon atoms) and, optionally, heteroatoms which can be n=N, S, or O. Additional exemplary proline phosphonate derivatives which contain a perfluoroalkyl group, a phenyl group or a substituted phenyl group and which can be used in accordance with the methods of the invention are those described in U.S. Pat. No. 5,543,396 (Powers '396). Other ketoamides, ketoacids and ketoesters that are useful reactive groups for reacting with the reactive center of a protease (e.g., a serine protease or a cysteine protease) are described in PCT/US91/09801, "Peptides, Ketoamides, Ketoacids, and Ketoesters", Applicant: Georgia Tech Research Corp. ("GA Tech") which claims priority to U.S. Pat. No. 635,287, filed Dec. 28, 1990.

In certain embodiments, the reactive groups are selected from the groups having the formulas,

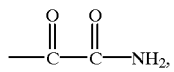

an alphaketo amide;

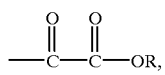

where R is an alkyl, or aryl group and may be substituted or unsubstituted, an alphaketo ester; and

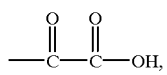

an alphaketo acid.

The reactive groups of the invention also include the reactive groups described in PCT/GB94/02615, "DPIV-Serine Protease Inhibitors" (Ferring). These include the above-noted boronyl groups [B(OH)$_2$], as well as pyrrolidides and the following reactive groups, any of which may be substituted or unsubstituted provided that the substitution does not adversely affect the functional activity of the reactive group or the binding moiety to which it is attached: CN, C≡C, CHO and CH=NPh, wherein Ph refers to phenyl. These examples are illustrative only and are not intended to limit the scope of the invention. As noted in Ferring, compounds containing these representative reactive groups can be prepared by an adaptation of the general route described by E. Schon et al., Biol, Chem. Hoppe-Seyler:372:305–311 (1991) and by W. W. Bachovchin et al., J. Biol. Chem. 265:3738–3743 (1990). (See, also, the above-referenced Bachovchin United States patents.)

The second targeting moiety, P$^2$, binds to a molecule that is present on the surface of the same or different cell to which the first targeting moiety binds. Preferably, the second targeting moiety binds to a molecule (e.g., a receptor, a major histocompatibility complex (MHC) molecule) which is present on the surface of a T cell or on the surface of a B cell. In certain embodiments, the second targeting moiety has a structure which mimics the substrate binding site of a protease that is present on a cell that is involved in immune system modulation. Thus, the second targeting moiety may be the same as the first targeting moiety, and the compounds of the invention are useful for crosslinking DPIV molecules on the same or different cells. For example, the compounds of the invention can be used to crosslink a first protease (e.g., a post-prolyl cleaving enzyme) on a first cell and a different protease (e.g., a trypsin, chymotrypsin, elastase or other serine protease or cysteine protease) that is expressed on the surface of the same or on a different second cell. In certain preferred embodiments, the first and second targeting moieties are identical (i.e., P$^2$=P$^1$) and the second reactive group R$^2$ may be absent (i.e., m=0), the same or different from the first reactive group R$^1$ (i.e., R$^1 \neq$R$^2$). Compounds which include identical P$^1$ and P$^2$ groups and identical R$^1$ and R$^2$ groups are referred to as "homoconjugates". In yet other embodiments, the first and second targeting moieties are different and these compounds are referred to as "heteroconjugates".

In yet other embodiments, the second targeting moiety is an antigen that selectively binds to an MHC molecule on the surface of an antigen presenting cell. Such embodiments of the invention are useful for antigen (e.g., tumor) -specific T cell expansion. Thus, according to a related aspect of the invention, the above-described DPIV inhibitors which include a second targeting moiety, P$^2$, that is an antigen (e.g., a tumor-specific antigen) can be used to generally stimulate hematopoietic progenitor cells (via the first targeting moiety, P$^1$) of the T cell lineage, as well as to specifically expand a subset of the population of peripheral blood T cells to obtain antigen-specific T cells. In particular, such compounds are useful for expanding such subsets of the T cell population to enrich for the antigen specific T cells. Thus, the invention provides an improved method which synergistically combines hematopoietic cell stimulation with antigen-specific T cell expansion ex vivo. This would be therapeutic for eliciting immune responses against residual tumor cells, metastatic cells, or to enhance the anti-tumor T cell activity in allogeneic transplants. It can also be used for ex vivo expansion of peripheral memory T cells specific for tumor antigens, pathogen antigens and other antigens associated with an adverse medical condition. Thus, the antigens that can be used in accordance with the foregoing methods include antigens characteristic of pathogens and cancer antigens.

The foregoing methods and compositions also are useful for ex vivo expansion of stem cells after transfection with retroviral or other vectors containing a heterologous nucleic acid (e.g., an antisense oligonucleotide, a nucleic acid encoding a therapeutic protein or peptide) for gene therapy applications. Stem cells into which a heterologous nucleic acid has been introduced ex vivo can be introduced into the subject using the known methods for implanting transfected cells into a human for gene therapy. See, e.g., U.S. Pat. No. 5,399,346 ("Gene Therapy") issued to Anderson et al.; PCT International application no. PCT/US92/01890 (Publication No. WO 92/15676, "Somatic Cell Gene Therapy", claiming priority to U.S. Ser. No. 667,169, filed Mar. 8, 1991, inventor I. M. Verma); PCT International application no. PCT/US89/05575 (Publication No. WO 90/06997, "Genetically Engineered Endothelial Cells and Use Thereof", claiming priority to U.S. Ser. No. 283,586, filed Dec. 8, 1989, inventors Anderson, W. F. et al.).

Antigens that are characteristic of tumor antigens typically will be derived from the cell surface, cytoplasm, nucleus, organelles and the like of cells of tumor tissue. Examples include antigens characteristic of tumor proteins, including proteins encoded by mutated oncogenes; viral proteins associated with tumors; and tumor mucins and glycolipids. Tumors include, but are not limited to, those from the following sites of cancer and types of cancer: lip, nasopharynx, pharynx and oral cavity, esophagus, stomach, colon, rectum, liver, gall bladder, biliary tree, pancreas, larynx, lung and bronchus, melanoma of skin, breast, cervix, uteri, uterus, ovary, bladder, kidney, brain and other parts of the nervous system, thyroid, prostate, testes, Hodgkin's disease, non-Hodgkin's lymphoma, multiple myeloma and leukemia. Viral proteins associated with tumors would be those from the classes of viruses noted above. Antigens characteristic of tumors may be proteins not usually expressed by a tumor precursor cell, or may be a protein which is normally expressed in a tumor precursor cell, but having a mutation characteristic of a tumor. An antigen characteristic of a tumor may be a mutant variant of the normal protein having an altered activity or subcellular distribution. Mutations of genes giving rise to tumor antigens, in addition to those specified above, may be in the coding region, 5' or 3' noncoding regions, or introns of a gene, and may be the result of point mutations, frameshifts, deletions, additions, duplications, chromosomal rearrangements and the like. One of ordinary skill in the art is familiar with the broad variety of alterations to normal gene structure and expression which gives rise to tumor antigens. Specific examples of tumor antigens include: proteins such as Ig-idiotype of B cell lymphoma, mutant cyclin-dependent kinase 4 of melanoma, Pmel-17 (gp 100) of melanoma, MART-1 (Melan-A) of melanoma, p15 protein of melanoma, tyrosinase of melanoma, MAGE 1, 2 and 3 of melanoma, thyroid medullary, small cell lung cancer, colon and/or bronchial squamous cell cancer, BAGE of bladder, melanoma, breast, and squamous cell carcinoma, gp75 of melanoma, oncofetal antigen of melanoma; carbohydrate/lipids such as muc1 mucin of breast, pancreas, and ovarian cancer, GM2 and GD2 gangliosides of melanoma; oncogenes such as mutant p53 of carcinoma, mutant ras of colon cancer and HER-2/neu proto-oncogene of breast carcinoma; viral products such as human papilloma virus proteins of squamous cell cancers of cervix and esophagus. It is also contemplated that proteinaceous tumor antigens may be presented by HLA molecules as specific peptides derived from the whole protein. Metabolic processing of proteins to yield antigenic peptides is well known in the art; for example see U.S. Pat. No. 5,342,774 (Boon et al.).

Preferred tumor antigens of the invention include the Melonoma tumor antigens (e.g., MAGE protein family (MAGE-1, MAGE-2, MAGE-3); MART-1 (peptide 27–35); and gp100); and the Colon carcinoma antigens (e.g., peptides of the mutated APC gene product). Particularly preferred Melanoma tumor antigen sequences are those reported by Slingluff et al., in Curr. Opin. in Immunol. 6:733–740 (1994):

| Gene/protein | MHC | Peptide | SEQ.ID NO. |
|---|---|---|---|
| MAGE-1 | A1 | EADPTGHSY | 1 |
|  | Cw1601 | SAYGEPRKL | 2 |
| MAGE-3 | A1 | EVDPIGHLY | 3 |
| Tyrosinase | A2 | MLLAVLYCL | 4 |
|  |  | YMNGTMSQV | 5 |
|  | A24 | — |  |
| gp100/pMel-17 | A2 | YLEPGPVTA | 6 |
|  |  | LLDGTATLRL | 7 |
| MART-1/Melan-A | A2 | AAGIGILTV | 8 |
|  |  | QDLTMKYQIF | 20 |

The MAGE protein family also reportedly has been associated with more than one type of carcinoma: MAGE-1 (Melanoma, thyroid medullary, and small-cell lung carcinoma), MAGE-2 (Melanoma, small-cell lung, colon, bronchial squamous cell, and thyroid medullary carcinoma), and MAGE-3 (Melanoma, small-cell lung, colon, bronchial squamous cell, and thyroid medullary carcinoma). See, also, Morioka, et al., "A Decapeptide (Gln-Asp-Leu-Thr-Met-Lys-Tyr-Gln-lle-Phe) from Human Melanoma Is Recognized by CTL in Melanoma Patients", J. Immunol. 153:5650 (1994), for additional tumor antigens (e.g., P1A, Connexin 37, MAGE-1, MAGE-3, MART 1/Aa, gp100, Tyrosinase) and/or information relating to the tissue distribution of selected tumor antigens.

Particularly preferred tumor antigens that are peptides of the mutated APC gene product are those reported by Townsend et al., in Nature 371:662 (1994)):

| Codon | Mutation | New Sequence | SEQ.ID No. |
|---|---|---|---|
| 298 | 2 bp del | SSST/LCTSKADKSSGNQGGNGVFIVVNAWYS | 9 |
| 540 | 1 bp del | SEDL/TAGYCKCFEEFVLASRCK | 10 |
| 1068 | 4 bp del | EQRQ/GIKVQLILFILRALMINTSSSNHIL DSRNVFLHTGHGEPMVQKQIEWVLIMELIKM | 11 |
| 1353 | 8 bp del | HKAV/FRSEISLQKWCSDTQKST | 12 |
| 1398 | 1 bp del | DSFE/SVRLPAPFRVNHAVEW | 13 |
| 1420 | 1 bp del | IISP/VIFQIALDKPCHQAEVKHLHHLLK QLKPSEKYLKIKHLLLKRERVDLSKLQ | 14 |
| 1439 | 1 bp del | RSKT/LHHLLKQLKPSEKYLKIKHLL LKRERVDLSKLQ | 15 |
| 1446 | 10 bp del | PPQT/GEKYLKIKHLLLKRERVDLSKLQ | 16 |
| 1488 | 1 bp del | DADT/YYILPRKVLQMDFLVHPA | 17 |
| 1490 | 1 bp del | DTLL/LLPRKVLQMDFLVHPA | 18 |
| 1493 | 11 bp del | LHFA/SRWIFLFIQPECSEPR | 19 |

In alternative embodiments, the second targeting moiety is a ligand that selectively binds to a receptor that is expressed on the surface of a cell (preferably a T cell or a B cell). Exemplary receptors which have naturally occurring ligands that can be mimicked by the second targeting moieties of the invention include receptors selected from the following group: CD2, TCR/C3, CD4, CD8, CD10, CD26, CD28, CD40, CD44, CD45, B7.1 and B7.2. According to yet other embodiments, the second targeting moiety is an antibody or antibody fragment that selectively binds to an epitope expressed on the cell surface. The epitope can be a portion of any of the foregoing receptors.

Regardless of the nature of the second targeting moiety target (e.g., protease, receptor, MHC complex, epitope), phage display and other types of combinatorial libraries can be screened in a manner analogous to that described above to identify non-naturally occurring targeting moieties that are useful in forming the compounds of the invention.

DPIV Inhibitors that do not Bind to the Active-site of DPIV (Non-active Site Binding Agents)

Non-active site DPIV binding agents are agents that: (i) selectively bind to DPIV at a location other than the active site and (ii) are capable of stimulating hematopoietic cells and/or thymocytes under the conditions described herein. Certain non-active site DPIV binding agents (e.g., non-competitive DPIV inhibitors) also inhibit the enzymatic activity of the DPIV. Inhibition of the enzymatic activity of DPIV can be assessed, for example, by measuring the proteolytic cleavage enzymatic activity of DPIV in the presence and absence of a putative DPIV inhibitor and determining whether the inhibitor inhibits such DPIV enzymatic activity. Preferably, such binding agents are isolated polypeptides which selectively bind the DPIV. Isolated binding polypeptides include antibodies and fragments of antibodies (e.g. Fab, $F(ab')_2$, Fd and antibody fragments which include a CDR3 region which binds selectively to the DPIV). Preferred isolated binding polypeptides are those that bind to an epitope that is at or near the catalytic site of the DPIV.

The invention, therefore, involves the use of antibodies or fragments of antibodies which have the ability to selectively bind to DPIV and stimulate hematopoietic cells and/or thymocytes under the conditions disclosed herein. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for $F(ab')_2$, Fab, Fv and Fd fragments; chimeric antibodies in which the Fc and/or FR and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies. Thus, the invention involves polypeptides of numerous size and type that bind specifically to DPIV and inhibit its functional activity. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptides and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent a completely degenerate or biased array. One then can select phage-bearing inserts which bind to the DPIV. This process can be repeated through several cycles of reselection of phage that bind to the DPIV. Repeated rounds lead to enrichment of phage bearing particular sequences. DNA sequence analysis can be conducted to identify the sequences of the expressed polypeptides. The minimal linear portion of the sequence that binds to DPIV can be determined. One can repeat the procedure using a biased library containing inserts containing part or all of the minimal linear portion plus one or more additional degenerate residues upstream or downstream thereof. Thus, DPIV, an extracellular domain thereof, or the like, can be used to screen peptide libraries, including phage display libraries, to identify and select peptide binding partners of the extracellular portion of DPIV. Such selected molecules then can be tested in screening assays which measure the ability of the binding agents to inhibit the functional activity of DPIV, e.g., the enzymatic functional activity of DPIV or to stimulate hematopoietic cell growth and/or differentiation.

The above-described binding agents which selectively bind DPIV are attached directly or indirectly (via a linker) to a culture vessel or other surface using the same types of chemical reactions described above in connection with the attachment of the DPIV active site inhibitors to such surfaces.

Linkers and Attachment of the Targeting Moiety, $P^1$

A linker is covalently coupled to the first and (optionally) second targeting moieties, $P^1$ and (optionally) $P^2$, in a manner that does not adversely affect the ability of these moieties to bind to their respective targeted binding partners. Preferably, such linkers further include a functional group for attaching the targeting moieties to a culture vessel, other surface, and/or additional targeting moieties. The preferred linker, L, has a length such that when it is positioned between one binding moiety and a second binding moiety or surface results in a minimum length of about 20 angstroms between the moieties or between the moiety and the surface. Preferably, this distance is from 20 to 60 angstroms, more preferably from 30 to 50 angstroms. Exemplary linkers, including a description of linker composition, size, and procedures for coupling the linker to the targeting moieties are provided below. In general, such linkers are commercially available (see, e.g., Pierce Catalog and Handbook, Rockford, Ill.) and are coupled to the targeting moieties using conventional coupling procedures which are well known to those of ordinary skill in the art.

In general, the linkers, L, contain at least two reactive groups. Homobivalent cross-linkers can contain two identical reactive groups, and heterobivalent crosslinkers contain two different reactive groups. Additional multivalent linkers are available which contain more than two reactive groups which can be the same (homomultivalent) or different (heteromultivalent). Typically, the linkers of the invention covalently couple the targeting moiety, $P^1$, via an amino or sulfhydryl group to the second targeting moiety or surface because such functional groups are commonly found in proteins and polymers that are used to form support materials for immobilizing proteins. Amine-reactive Groups include imido esters and N-hydroxysuccinimidyl (NHS) esters. Sulfhydryl-reactive Groups include maleimides, alkyl and aryl halides, α-haloacetyls and pyridyl disulfides. The majority of commercially available heterobivalent cross-linkers contain an amine-reactive functional group. Cross-linkers that are amine-reactive at one end and sulfhydryl-reactive at the other end are quite common. Other linkers are commercially available which covalently attach the targeting moiety $P^1$ to another targeting moiety, surface, or additional targeting moiety via reactive groups other than amino or sulfhydryl groups, for example, via hydroxyls, carboxyls, phenols or carbohydrate groups. Carbodiimides also can be used to couple carboxyls to primary amines or hydrazides, resulting in formation of amide or hydrazone bonds.

Attachment of Targeting Moiety, $P^1$, to a Culture Vessel or Other Surface Proteins, peptides and other molecules can be immobilized on solid-phase matrices for use in accordance with the methods of the invention. The matrices may be agarose, beaded polymers, polystyrene plates or balls, porous glass or glass slides, and nitrocellulose or other membrane materials. Some supports can be activated for direct coupling to a ligand. Other supports are made with nucleophiles or other functional groups that can be linked to proteins or other ligands using cross-linkers.

Immobilization of the DPIV inhibitors of the invention to solid-supports can be accomplished using routine coupling chemistries. In general, the compounds of the invention are immobilized by including in the compounds an accessible first functional group (e.g., an alcohol group) and contacting the compound with a solid-support containing a complementary second functional group (e.g., carboxyl groups) under conditions and for a period of time sufficient to permit the first and the second functional groups to react with one another to form a covalent bond (e.g., ester bond). By "accessible" in reference to a functional group, it is meant that the functional group is in a form which is reactive and is not sterically precluded from reacting with the solid-support. Attachment can be direct or indirect (i.e., via a linker, L).

The functional groups for immobilizing the compounds of the invention to a solid-support can be introduced into the peptide binding moieties or the linker portions of these compounds. For example, amino acids that include functional groups in their side chains (e.g., aspartate, glutamate, cysteine residues) can be incorporated into the peptide binding moiety during synthesis and positioned at a sufficient distance from the reactive group which binds to the target protein to avoid unwanted steric hindrance by the solid-support in the reaction between the compound and its target protein. Alternatively, the compounds of the invention can be immobilized via a functional group in the linker molecule to a solid-support. Thus, for example, the linkers which are used in this aspect of the invention can include, in addition to the first and the second linker reactive groups for binding to the first and the second peptide binding moieties, a further functional group for binding to the solid support. An exemplary multivalent (trivalent) linker of this type is illustrated below. Such multivalent linkers are commercially available and can be synthesized by one of ordinary skill in the art using no more than routine experimentation:

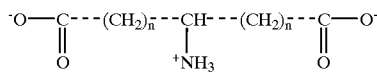

To prevent side reactions, it is preferred that the linker reactive groups that are used for coupling the linker molecule to the peptide binding moieties be different from functional groups that are used for coupling the linker to the solid-support. Such functional groups can be introduced into the linker molecules at any time during or after the synthesis of these molecules. Thus, in general, the same types of functional groups, protection/deprotection reactions and reagents, and reaction conditions that are established in the art for using linker molecules to couple, e.g., proteins or peptides to one another or to solid supports can be used for immobilizing the compounds of the invention to a solid support.

Included at the end of the detailed description are tables showing a representative sampling of commercially available cross-linkers, e.g., from Pierce Catalog and Handbook, Rockford, Ill. The table also identifies which group the linker is reactive towards, e.g., sulfhydryls, carboxyls.

Culture Vessels and Surfaces

A variety of culture vessels can be used. Commercially available incubation vessels include stirring flasks (Corning, Inc., Corning, N.Y.), stirred tank reactors (Verax, Lebanon, N.H.), airlift reactors, suspension cell reactors, cell adsorption reactors and cell entrapment reactors, petri dishes, multiwell plates, flasks, bags and hollow fiber devices, cell foam (Cytomatrix), maxisorb plates (NUNC), and cell culture systems (e.g., Aastrom Cell Production System, see also U.S. Pat. No. 5,635,386, entitled "Methods for regulating the specific lineages of cells produced in a human hematopoietic cell culture", issued to Palsson et al., and U.S. Pat.

No. 5,646,043, entitled "Methods for the ex vivo replication of human stem cells and/or expansion of human progenitor cells", issued to Emerson, et al.). The Aastrom culture devise is an incubation chamber for expansion of human stem cells ex vivo using a specific medium exchange culture system. The device reportedly is useful for expanding all types of hematopoietic cells including, e.g., stem cells, progenitor cells, stromal cells, but excluding lymphoid cells. In general, the cell cultures using the above-noted culture vessels are maintained in suspension by a variety of techniques including stirring, agitation or suspension by means of beads. In general, such vessels are formed of one or more of the following components: polystyrene, polypropylene, acrylic, nylon, and glass. For those embodiments in which the first targeting moiety $P^1$ is attached to a vessel surface, conventional immobilization techniques are utilized to attach the moiety to the surface, either directly or via linker, L.

The insoluble matrices listed above do not themselves possess functional groups for the attachment of compounds of the invention, and must therefore be chemically modified, a process known as activation. For example, polystyrene can be activated chloromethylation of the phenyl residues (Pierce Chemical Company Catalog and Handbook; *Combinatorial Peptide & Nonpeptide Libraries*. A Handbook VCH Weinheim Ed. Giuntha Jung—1996—Chapter 16 & 17) to yield chloromethyl polystyrene. Advantage can then be taken of the reactive benzylic chloride functional group to introduce carboxylate, amino, hydroxyl, maleimide, sulfhydryl, N-succinimidyl, and many other functional groups. The introduction of the functional groups then permits chemistries to be carried out which permit the covalent attachment of compounds of the invention either directly or through a linker spacer unit. The linking reactions require compatible functional groups on the matrix and the ligand or spacer-linker group which is or will be attached to the compound of the invention. For example, introduction of a carboxylate group on the matrix permits covalent coupling to free amino groups. A polystyrene derivatized to carry carboxylate groups can be covalently attached directly to Lys-boroPro through coupling to the free ε amino group of the Lys side chain, or through a spacer linker which has a free amino group. Alternatively, a polystyrene derivatized to carry an amino group can be attached to, for example, Lys-boroPro through coupling via a spacer linker containing two carboxylate groups, one to couple to the ε amino group of Lys-boroPro, the other to the amino group of the amino-derivatized polystyrene.

The chemistry leading to such coupling are well-known and described in many sources including in the catalogues of companies such as Pierce Chemical which sells both the matrices, activated and unactivated, and linker-spacer molecules. Other supplies include for Sigma, Novabiochem, among others. Methods for attaching ligands as described above for polystyrene but specific for the other matrices listed above are available, well known, and described in sources such as those described above and *Immobilized Affinity Ligand Techniques*. "All the 'recipes' for successful affinity matrix preparation"; *Chemistry of Protein Conjugation and Cross-linking*, by Shan S. Wong.

The matrices are available in several forms including as beads, and magnetic beads which provide for especially easy removal of the matrix-attached ligand.

Avidin-Biotin chemistry provides another way of achieving the same end result, the attachment of the compounds of the invention to insoluble matrices. Biotin can easily be attached to the ε amino group of Lys-boroPro for example and the resulting conjugate will adhere with high affinity to avidin or strepavidin. A wide assortment of insolubilized derivatives of avidin and strepavidin are available commercially (*Avidin-Biotin Chemistry. A Handbook*—Developed by Pierce Technical Assistance experts).

Alternatively, the targeting moiety, $P^1$, can be attached to a particulate form (e.g., a particle or a membrane) that has a surface to which the targeting moiety can be directly or indirectly attached. Exemplary materials that can be used to form such particulates include nitrocellulose, agarose, sepharose, and other types of support materials to which ligands are routinely attached to, e.g., form affinity chromatography materials. In the perferred embodiments, the particulate is a magnetic particle such as described in U.S. Pat. No. 4,554,088, issued to Whitehead et al., entitled "Magnetic particles for use in separations"; U.S. Pat. No. 5,382, 468, issued to Chagnon et al., entitled "Biodegradable magnetic microclusters and methods for making them"; U.S. Pat. No. 4,454,234, issued to Czerlinkski, entitled "Coated magnetizable microparticles, reversible suspensions thereof, and processes related thereto"; U.S. Pat. No. 4,795,698, issued to Owen et al, entitled "Magnetic-polymer particles"; and U.S. Pat. No. 4,582,622, issued to Ikeda et al, entitled "Magnetic particulate for immobilization of biological protein and process of producing the same".

According to yet another aspect of the invention, an apparatus for practicing the above-described method is provided. The apparatus includes a container; and an inhibitor of DPIV contained therein or attached thereto. Preferably, the container is a sterile container. The DPIV inhibitor can be in soluble or insoluble form as described above. Thus, for example, the DPIV inhibitor can be present in the container in a dry state (e.g., lyophilized), unbound or attached to the surface of the container, and sold to the end user in sterile form to minimize the likelihood of contamination by the end user (e.g., when introducing the inhibitor to the container) and to further minimize the likelihood of loss of activity of the inhibitor (e.g., by providing the inhibitor in a dry state that is less likely to lose activity upon storage). Alternatively, the DPIV inhibitor can be attached to a particle, such as a magnetic particle, which particle then can be sold in a dry state in a separate vessel or provided in the container for cell culture.

According to still another aspect of the invention, a kit for stimulating the growth and/or differentiation of hematopoietic cells in vitro is provided. The kit includes the above-described apparatus, together with instructions for using the apparatus to stimulate the growth and/or differentiation of hematopoietic cells in vitro. Optionally, the kit further contains the appropriate additional growth nutrients for culturing the hematopoietic cells. Such nutrients can be provided in liquid or dry state in the container of the apparatus or in a separate container, the contents of which can be added to the apparatus container at the time of culturing the cells.

According to still another aspect of the invention, a method for stimulating hematopoietic cells and expanding antigen-specific T cells in vitro is provided. The stimulating and expansion steps can be performed concurrently or sequentially. Three embodiments of this method are described below to illustrate this method. In general, the embodiments differ from one another in the selection of the hematopoietic cells that are stimulated in vitro. In each embodiment, the culturing step(s) can be performed in the presence or absence of added cytokines or stromal cells. The preferred heteroconjugates that are used in each embodiment contains a tumor-specific antigen or a pathogen-specific antigen.

The first embodiment of the method for obtaining antigen-specific T cells involves stimulating bone marrow cells in culture. The bone marrow cells in culture may include a mixture of cells; however, preferably, the bone marrow cells in culture are isolated CD34+ cells or isolated stem cells. According to this embodiment, the method involves: (1) culturing the bone marrow cells in the presence of a sufficient amount of a DPIV inhibitor (e.g., a DPIV monomer and/or homoconjugate) to expand the number of early T lineage cells in culture; and (2) culturing the early T lineage cells with a sufficient amount of a heteroconjugate containing an inhibitor of a DPIV inhibitor attached to an antigenic peptide (e.g., a tumor- or pathogen-specific antigen) to expand the number of antigen-specific T cells in the culture. Step (2) can be performed in the presence or absence of the specific antigen. Steps (1) and (2) can be performed concurrently or sequentially. In general, the number of antigen-specific T cells is compared to a control culture of bone marrow cells that is treated as described in steps (1) and (2) with the exception that the control culture is not contacted with the heteroconjugate. At each step, the cells are cultured in the presence of the DPIV inhibitor or heteroconjugate for a time sufficient to increase the number of early T lineage cells and to expand the number of antigen-specific T cells, respectively, relative to the numbers of such cells that are present in the control culture.

The second embodiment is directed to stimulating umbilical cord blood cells in culture. This embodiment involves: (1) culturing the umbilical cord blood cells in the presence of a sufficient amount of a DPIV inhibitor (e.g., a DPIV monomer and/or homoconjugate) to expand the number of early T lineage cells in culture; and (2) culturing the early T lineage cells with a heteroconjugate containing an inhibitor of a DPIV inhibitor attached to an antigenic peptide (e.g., a tumor- or pathogen-specific antigen) to expand the number of antigen-specific T cells that are present in the culture. Step (2) can be performed in the presence or absence of the specific antigen. Steps (1) and (2) can be performed concurrently or sequentially. In general, the number of antigen-specific T cells is compared to a control culture of umbilical cord blood cells that is treated as described in steps (1) and (2) with the exception that the control culture is not contacted with the heteroconjugate. At each step, the cells are cultured in the presence of the DPIV inhibitor or heteroconjugate for a time sufficient to increase the number of early T lineage cells and to expand the number of antigen-specific T cells, respectively, relative to the numbers of such cells that are present in the control culture.

The third embodiment is directed to stimulating peripheral blood stem cells in culture. This embodiment involves: (1) culturing the peripheral blood stem cells in the presence of a sufficient amount of a DPIV inhibitor (e.g., a DPIV monomer and/or homoconjugate) to expand the number of T cells in culture; and (2) culturing the T cells with a sufficient amount of a heteroconjugate containing an inhibitor of a DPIV inhibitor attached to an antigenic peptide (e.g., a tumor- or pathogen-specific antigen) to expand the number of antigen-specific T cells in the culture. Step (2) can be performed in the presence or absence of the specific antigen. Steps (1) and (2) can be performed concurrently or sequentially. In general, the number of antigen-specific T cells is compared to a control culture of peripheral blood stem cells that is treated as described in steps (1) and (2) with the exception that the control culture is not contacted with the heteroconjugate. At each step, the cells are cultured in the presence of the DPIV inhibitor or heteroconjugate for a time sufficient to increase the number of T cells and to expand the number of antigen-specific T cells, respectively, relative to the numbers of such cells that are present in the control culture. Alternatively, because peripheral blood is known to contain T cells, it is possible to expand the number of antigen-specific T cells in culture without the stimulation step (1), i.e., the method for expanding the number of antigen-specific T cells involves culturing the peripheral blood cells with a sufficient amount of a heteroconjugate containing an inhibitor of a DPIV inhibitor attached to an antigenic peptide (e.g., a tumor- or pathogen-specific antigen) to expand the number of antigen-specific T cells in the culture. This step can be performed in the presence or absence of the specific antigen.

EXAMPLES

An exemplary procedure for contacting several representative DPIV inhibitors is provided below.

| Experimental Protocol |
|---|
| 1. Obtain bone marrow or umbilical cord blood in heparinized (green top) tube. Can be stored at room temperature until use within 48 hours. |
| 2. Mix marrow/blood 1:1 with phosphate-buffered saline, pH 7.4(PBS) that has been stored at 4° C. |
| 3. Carefully layer blood-PBS mixture on a 2x volume quantity of Histopaque (Sigma) that has been stored at 4° C. |
| 4. Centrifuge at 400 g × 20 minutes at 37° C. |
| 5. Carefully collect cells at interface and wash x2 in cold PBS. |
| 6. Count viable cells using trypan blue. |
| 7. Set up cells as 1 ml cultures in plastic culture tubes (or 96 well or 24 well microtiter plates) at $10^4$ cells/ml in CellGro Iscove's Modified Dulbecco's medium (Meditech) containing kanamycin (5 ug/ml), desired concentration of Xaa-boroPro or other compound of the invention, and the absence or presence of Giant Cell Tumor-Conditioned Medium (GCT-CM, Origen) as source of growth factors. Xaa-boroPro or other compounds of the invention should be diluted to medium and added to culture only after cells are in culture tube. |
| 8. Cells are cultured at 37° C. in a moist air incubator containing 5% $CO_2$. |
| 9. At desired time, an aliquot of cells are removed and counted. |
| 10. Counting can be performed under the microscope (direct) or by using the MTT assay (colorimetric assay). |

The results of experiments which employed this protocol are illustrated in the figures attached hereto and are described in the brief description of the drawings.

All patents, patent publications and other documents that are identified in this application are incorporated in their entirety herein by reference.

Those skilled in the art will recognize, or be able to ascertain using no more than routine experimentation, many equivalents to the specific embodiments of the invention described herein. Such equivalents are intended to be encompassed by the following claims.

The Tables are presented below and are followed by what is claimed, the Abstract, and the Sequence Listing.

REACTIVITY OF COMMERCIALLY AVAILABLE CROSS-LINKERS

| Double-Agent Cross-linker Acronym | —NH$_2$ Aminos | —SH Sulfhydryls | Carbohydrates | Non-selective (Photo-reactive) | —COOH Carboxyls | Thiols | Base | Periodate | Hydroxylomine |
|---|---|---|---|---|---|---|---|---|---|
| Sulfo-SAMC | X | | | X | | | | | |
| Sulfo-SANPAH | X | | | X | | | | | |
| Sulfo-SAPB | X | | | X | | | | | |
| Sulfo-SIAB | X | X | | | | | | | |
| Sulfo-SMCC | X | X | | | | | | | |
| Sulfo-SMBP | X | X | | | | | | | |
| Sulfo-LC-SMPT | X | X | | | | | | | |
| SANPAH | X | | | X | | | | | |
| SASD | X | | | X | | X | | | |
| SDBP | X | | | | | | | | |
| SIAB | X | X | | | | | | | |
| SMCC | X | X | | | | | | | |
| SMBP | X | X | | | | | | | |
| SMPT | X | X | | | | | | | |
| SPDP | X | X | | | | X | | | |
| Sulfo-BSOCOES | X | | | | | | X | | |
| Sulfo-DST | X | | | | | | | X | |
| Sulfo-EGS | X | | | | | | | | X |
| Sulfo-GMBS | X | X | | | | | | | |
| Sulfo-HSAB | X | | | X | | | | | |
| Sulfo-LC-SPDP | X | X | | | | X | | | |
| Sulfo-MBS | X | X | | | | | | | |
| Sulfo-NHS-ASA | X | | | X | | | | | |
| Sulfo-NHS-LC-ASA | X | | | X | | | | | |
| Sulfo-SADP | X | | | X | | X | | | |
| DSS | X | | | | | | | | |
| DST | X | | | | | | | X | |
| DTBP | X | | | | | X | | | |
| DTSSP | X | | | | | X | | | |
| EDC | X | | | | X | | | | |
| FGS | X | | | | | | | | X |
| GMBS | X | X | | | | | | | |
| HSAB | X | | | X | | | | | |
| LC-SPDP | X | X | | | | | | | |
| MBS | X | X | | | | X | | | |
| M$_2$C$_2$H | | X | X | | | | | | |
| MPBH | | X | X | | | | | | |
| NHS-ASA | X | | | X | | | | | |
| PDPH | | X | X | | | X | | | |
| PNP-DTP | X | | | X | | | | | |
| SADP | X | | | X | | X | | | |
| SAED | X | | | X | | X | | | |
| SAND | X | | | X | | X | | | |
| ABH | | | X | X | | | | | |
| ANB-NOS | X | | | X | | | | | |
| APDP | | X | | X | | X | | | |
| APG | | | | X | | | | | |
| ASIB | | X | | X | | | | | |
| ASBA | | | | X | X | | | | |
| BASED | | | | X | | X | | | |
| BS$^3$ | X | | | | | | | | |
| BMH | | X | | | | | | | |
| BSOCOES | X | | | | | | X | | |
| DFDNB | X | | | | | | | | |
| DMA | X | | | | | | | | |
| DMP | X | | | | | | | | |
| DMS | X | | | | | | | | |
| DPDPB | | X | | | | X | | | |

-continued

REACTIVITY OF COMMERCIALLY AVAILABLE CROSS-LINKERS

| Double-Agent Cross-linker | Reactive Towards | | | | | Cleavable By | | | |
|---|---|---|---|---|---|---|---|---|---|
| Acronym | —NH$_2$ Aminos | —SH Sulfhydryls | Carbohydrates | Non-selective (Photo-reactive) | —COOH Carboxyls | Thiols | Base | Periodate | Hydroxylomine |
| DSG | X | | | | | | | | |
| DSP | X | | | | | X | | | |

What is claimed is:

1. A method for expanding antigen-specific T cells in vitro, comprising:
   (1) culturing bone marrow cells in the presence of a sufficient amount of a DPIV inhibitor that is a monomer or a homoconjugate to expand the number of early T lineage cells in the culture; and
   (2) culturing the early T lineage cells in the presence of a sufficient amount of a heteroconjugate containing a DPIV inhibitor attached to an antigenic peptide to expand the number of antigen-specific T cells in the culture.

2. The method of claim 1, wherein the DPIV inhibitor is selected from the group consisting of a DPIV monomer, a DPIV homoconjugate, and a combination of the foregoing.

3. The method of claim 1, wherein the heteroconjugate contains a tumor-specific antigen.

4. The method of claim 1, wherein the heteroconjugate contains a pathogen-specific antigen.

5. The method of claim 1, wherein step (1) and step (2) are performed sequentially.

6. The method of claim 1, wherein the bone marrow cells are selected from the group consisting of isolated CD34+ cells and isolated stem cells.

7. A method for expanding antigen-specific T cells in vitro, comprising:
   (1) culturing umbilical cord blood cells in the presence of a sufficient amount of a DPIV inhibitor that is a monomer or a homoconjugate to expand the number of early T lineage cells in the culture; and
   (2) culturing the early T lineage cells in the presence of a sufficient amount of a heteroconjugate containing a DPIV inhibitor attached to an antigenic peptide to expand the number of antigen-specific T cells in the culture.

8. A method for expanding antigen-specific T cells in vitro, comprising:
   (1) culturing peripheral blood cells in the presence of a sufficient amount of a DPIV inhibitor that is a monomer or a homoconjugate to expand the number of T cells in the culture; and
   (2) culturing the T cells with a sufficient amount of a heteroconjugate containing a DPIV inhibitor attached to an antigenic peptide to expand the number of antigen-specific T cells in the culture.

9. A method for expanding antigen-specific T cells in vitro, comprising:
(1) culturing peripheral blood cells in the presence of a sufficient amount of a heteroconjugate containing a DPIV inhibitor attached to an antigenic peptide to expand the number of antigen-specific T cells in the culture.

10. The method of claim 9, wherein the culturing is performed in the presence of added cytokines or stromal cells.

11. The method of claim 9, wherein the culturing is performed in the absence of added cytokines or stromal cells.

12. The method of claim 9, wherein the culturing is performed in the presence of the antigenic peptide.

13. A method for expanding antigen-specific T cells in vitro, comprising:
culturing peripheral blood cells in the presence of a sufficient amount of a heteroconjugate containing a DPIV inhibitor attached to an antigenic peptide to expand the number of antigen-specific T cells in the culture and in the presence of the antigenic peptide.

14. A method for expanding antigen-specific T cells in vitro, comprising:
(1) culturing hematopoietic precursor cells in the presence of a sufficient amount of a DPIV inhibitor to expand the number of early T lineage cells in the culture; and
(2) culturing the early T lineage cells in the presence of a sufficient amount of a heteroconjugate containing a DPIV inhibitor attached to an antigenic peptide to expand the number of antigen-specific T cells in the culture,
wherein the hematopoietic precursor cells are bone marrow cells or umbilical cord blood cells, and
wherein at least one culturing step is performed in the presence of added cytokines or stromal cells.

15. A method for expanding antigen-specific T cells in vitro, comprising:
(1) culturing hematopoietic precursor cells in the presence of a sufficient amount of a DPIV inhibitor to expand the number of early T lineage cells in the culture; and
(2) culturing the early T lineage cells in the presence of a sufficient amount of a heteroconjugate containing a DPIV inhibitor attached to an antigenic peptide to expand the number of antigen-specific T cells in the culture,
wherein the hematopoietic precursor cells are bone marrow cells or umbilical cord blood cells, and
wherein at least one culturing step is performed in the absence of added cytokines or stromal cells.

16. A method for expanding antigen-specific T cells in vitro, comprising:
(1) culturing hematopoietic precursor cells in the presence of a sufficient amount of a DPIV inhibitor to expand the number of early T lineage cells in the culture; and
(2) culturing the early T lineage cells in the presence of a sufficient amount of a heteroconjugate containing a DPIV inhibitor attached to an antigenic peptide to expand the number of antigen-specific T cells in the culture,
wherein the hematopoietic precursor cells are bone marrow cells or umbilical cord blood cells, and
wherein step (2) is performed in the presence of the antigenic peptide.

17. A method for expanding antigen-specific T cells in vitro, comprising:
(1) culturing peripheral blood cells in the presence of a sufficient amount of a DPIV inhibitor to expand the number of T cells in the culture; and
(2) culturing the T cells in the presence of a sufficient amount of a heteroconjugate containing a DPIV inhibitor attached to an antigenic peptide to expand the number of antigen-specific T cells in the culture,
wherein at least one culturing step is performed in the presence of added cytokines or stromal cells.

18. A method for expanding antigen-specific T cells in vitro, comprising:
(1) culturing peripheral blood cells in the presence of a sufficient amount of a DPIV inhibitor to expand the number of T cells in the culture; and
(2) culturing the T cells in the presence of a sufficient amount of a heteroconjugate containing a DPIV inhibitor attached to an antigenic peptide to expand the number of antigen-specific T cells in the culture,
wherein at least one culturing step is performed in the absence of added cytokines or stromal cells.

19. A method for expanding antigen-specific T cells in vitro, comprising:
(1) culturing peripheral blood cells in the presence of a sufficient amount of a DPIV inhibitor to expand the number of T cells in the culture; and
(2) culturing the T cells in the presence of a sufficient amount of a heteroconjugate containing a DPIV inhibitor attached to an antigenic peptide to expand the number of antigen-specific T cells in the culture,
wherein step (2) is performed in the presence of the antigenic peptide.

* * * * *

SEQUENCE LISTING

<160> NUMBER OF SEQ ID NOS: 20

<210> SEQ ID NO 1
<211> LENGTH: 9
<212> TYPE: PRT
<213> ORGANISM: homo sapiens

<400> SEQUENCE: 1

Glu Ala Asp Pro Thr Gly His Ser Tyr
1               5

<210> SEQ ID NO 2
<211> LENGTH: 9
<212> TYPE: PRT
<213> ORGANISM: homo sapiens

<400> SEQUENCE: 2

Ser Ala Tyr Gly Glu Pro Arg Lys Leu
1               5

<210> SEQ ID NO 3
<211> LENGTH: 9
<212> TYPE: PRT
<213> ORGANISM: homo sapiens

<400> SEQUENCE: 3

Glu Val Asp Pro Ile Gly His Leu Tyr
1               5

<210> SEQ ID NO 4
<211> LENGTH: 9
<212> TYPE: PRT
<213> ORGANISM: homo sapiens

<400> SEQUENCE: 4

Met Leu Leu Ala Val Leu Tyr Cys Leu
1               5

<210> SEQ ID NO 5
<211> LENGTH: 9
<212> TYPE: PRT
<213> ORGANISM: homo sapiens

<400> SEQUENCE: 5

Tyr Met Asn Gly Thr Met Ser Gln Val
1               5

<210> SEQ ID NO 6
<211> LENGTH: 9

```
<212> TYPE: PRT
<213> ORGANISM: homo sapiens

<400> SEQUENCE: 6

Tyr Leu Glu Pro Gly Pro Val Thr Ala
1               5

<210> SEQ ID NO 7
<211> LENGTH: 10
<212> TYPE: PRT
<213> ORGANISM: homo sapiens

<400> SEQUENCE: 7

Leu Leu Asp Gly Thr Ala Thr Leu Arg Leu
1               5                   10

<210> SEQ ID NO 8
<211> LENGTH: 9
<212> TYPE: PRT
<213> ORGANISM: homo sapiens

<400> SEQUENCE: 8

Ala Ala Gly Ile Gly Ile Leu Thr Val
1               5

<210> SEQ ID NO 9
<211> LENGTH: 31
<212> TYPE: PRT
<213> ORGANISM: homo sapiens

<400> SEQUENCE: 9

Ser Ser Ser Thr Leu Cys Thr Ser Lys Ala Asp Lys Ser Ser Gly Asn
1               5                   10                  15

Gln Gly Gly Asn Gly Val Phe Ile Val Val Asn Ala Trp Tyr Ser
            20                  25                  30

<210> SEQ ID NO 10
<211> LENGTH: 22
<212> TYPE: PRT
<213> ORGANISM: homo sapiens

<400> SEQUENCE: 10

Ser Glu Asp Leu Thr Ala Gly Tyr Cys Lys Cys Phe Glu Phe Val
1               5                   10                  15

Leu Ala Ser Arg Cys Lys
            20

<210> SEQ ID NO 11
<211> LENGTH: 60
<212> TYPE: PRT
<213> ORGANISM: homo sapiens

<400> SEQUENCE: 11

Glu Gln Arg Gln Gly Ile Lys Val Gln Leu Ile Leu Phe Ile Leu Arg
1               5                   10                  15

Ala Leu Met Ile Asn Thr Ser Ser Asn His Ile Leu Asp Ser Arg
            20                  25                  30

Asn Val Phe Leu His Thr Gly His Gly Glu Pro Met Val Gln Lys Gln
                35                  40                  45

Ile Glu Trp Val Leu Ile Met Glu Leu Ile Lys Met
    50                  55                  60
```

```
<210> SEQ ID NO 12
<211> LENGTH: 22
<212> TYPE: PRT
<213> ORGANISM: homo sapiens

<400> SEQUENCE: 12

His Lys Ala Val Phe Arg Ser Glu Ile Ser Leu Gln Lys Trp Cys Ser
 1               5                  10                  15

Asp Thr Gln Lys Ser Thr
            20

<210> SEQ ID NO 13
<211> LENGTH: 20
<212> TYPE: PRT
<213> ORGANISM: homo sapiens

<400> SEQUENCE: 13

Asp Ser Phe Glu Ser Val Arg Leu Pro Ala Pro Phe Arg Val Asn His
 1               5                  10                  15

Ala Val Glu Trp
            20

<210> SEQ ID NO 14
<211> LENGTH: 55
<212> TYPE: PRT
<213> ORGANISM: homo sapiens

<400> SEQUENCE: 14

Ile Ile Ser Pro Val Ile Phe Gln Ile Ala Leu Asp Lys Pro Cys His
 1               5                  10                  15

Gln Ala Glu Val Lys His Leu His His Leu Leu Lys Gln Leu Lys Pro
             20                  25                  30

Ser Glu Lys Tyr Leu Lys Ile Lys His Leu Leu Leu Lys Arg Glu Arg
         35                  40                  45

Val Asp Leu Ser Lys Leu Gln
     50                  55

<210> SEQ ID NO 15
<211> LENGTH: 37
<212> TYPE: PRT
<213> ORGANISM: homo sapiens

<400> SEQUENCE: 15

Arg Ser Lys Thr Leu His His Leu Leu Lys Gln Leu Lys Pro Ser Glu
 1               5                  10                  15

Lys Tyr Leu Lys Ile Lys His Leu Leu Leu Lys Arg Glu Arg Val Asp
             20                  25                  30

Leu Ser Lys Leu Gln
         35

<210> SEQ ID NO 16
<211> LENGTH: 27
<212> TYPE: PRT
<213> ORGANISM: homo sapiens

<400> SEQUENCE: 16

Pro Pro Gln Thr Gly Glu Lys Tyr Leu Lys Ile Lys His Leu Leu Leu
 1               5                  10                  15

Lys Arg Glu Arg Val Asp Leu Ser Lys Leu Gln
             20                  25
```

```
<210> SEQ ID NO 17
<211> LENGTH: 22
<212> TYPE: PRT
<213> ORGANISM: homo sapiens

<400> SEQUENCE: 17

Asp Ala Asp Thr Tyr Tyr Ile Leu Pro Arg Lys Val Leu Gln Met Asp
1               5                   10                  15

Phe Leu Val His Pro Ala
            20

<210> SEQ ID NO 18
<211> LENGTH: 20
<212> TYPE: PRT
<213> ORGANISM: homo sapiens

<400> SEQUENCE: 18

Asp Thr Leu Leu Leu Leu Pro Arg Lys Val Leu Gln Met Asp Phe Leu
1               5                   10                  15

Val His Pro Ala
            20

<210> SEQ ID NO 19
<211> LENGTH: 20
<212> TYPE: PRT
<213> ORGANISM: homo sapiens

<400> SEQUENCE: 19

Leu His Phe Ala Ser Arg Trp Ile Phe Leu Phe Ile Gln Pro Glu Cys
1               5                   10                  15

Ser Glu Pro Arg
            20

<210> SEQ ID NO 20
<211> LENGTH: 10
<212> TYPE: PRT
<213> ORGANISM: homo sapiens

<400> SEQUENCE: 20

Gln Asp Leu Thr Met Lys Tyr Gln Ile Phe
1               5                   10
```